United States Patent [19]

Snyderman et al.

[11] Patent Number: 4,822,606
[45] Date of Patent: Apr. 18, 1989

[54] IMMUNOSUPPRESSIVE SYNTHETIC PEPTIDES AND ANALOGS THEREOF BASED ON RETROVIRAL ENVELOPE SEQUENCES

[75] Inventors: Ralph D. Snyderman; George J. Cianciolo, both of Durham, N.C.

[73] Assignee: Duke University, Durham, N.C.

[21] Appl. No.: 848,469

[22] Filed: Apr. 7, 1986

[51] Int. Cl.$^4$ .................. A61K 39/12; C07K 7/08; C07K 7/10
[52] U.S. Cl. .................................... 424/88; 530/324; 530/326; 530/345; 530/350; 530/403
[58] Field of Search ............... 530/324, 326, 345, 350, 530/403; 424/88

[56] References Cited

FOREIGN PATENT DOCUMENTS 0114759 8/1984 European Pat. Off. .

OTHER PUBLICATIONS

Cianciolo et al, Nature, vol. 311, p. 515 (1984).
Goodman, Basic & Clinical Immunology, Lange Medical publications, edited by Fudenberg et al., pp. 32–33 (1976).
Science, (1985), vol. 230, pp. 453–455, by George J. Cianciolo et al, "Inhibition of Lymphocyte Proliferation by a Syntheric Peptide Homologous to Retorviral Envelope Proteins".

Primary Examiner—Delbert R. Phillips
Assistant Examiner—Christina Chan
Attorney, Agent, or Firm—Oblon, Fisher, Spivak, McClelland & Maier

[57] ABSTRACT

Novel peptides having immunosuppressive or immunoregulatory activity are disclosed.

35 Claims, 13 Drawing Sheets

IMMUNOSUPPRESSIVE SYNTHETIC PEPTIDES AND ANALOGS THEREOF BASED ON RETROVIRAL ENVELOPE SEQUENCES

BACKGROUND OF THE INVENTION

1. Field of the Invention:

This invention relates to immunomodulation and immunodiagnosis.

2. Discussion of the Background:

This invention relates to the area of regulation of immune responsiveness in various disease states or in patients undergoing organ transplantations. It also relates to the area of immunogen development for naturally-occurring immunosuppressive factors associated with disease states (e.g., cancer, retroviral infections, viral infections, arthritis, etc.)

Immunological reactions can destroy neoplastic cells in vivo, and the accumulation of macrophages within a tumor can lead to its destruction. Cytotoxic T lymphocytes, natural killer (NK) cells, and activated macrophages can kill tumor cells in vitro. These observations suggest that the immune system provides some resistance against the development and spread of cancer, a contention strengthened by increased incidence of spontaneous tumors in individuals with congenital or acquired immune deficiency diseases.

In animals infected by tumor-producing retroviruses immunosuppression frequently precedes the development of tumors and a causal relationship is suspected between infection by the human retroviruses named T-cell lymphotropic virus III (HTLV III) or lymphadenopathy-associated retrovirus (LAV) and the development of the acquired immune deficiency syndrom (AIDS) and Kaposi's sarcoma.

Since immune mechanisms may limit the development or spread of cancer, clinically apparent tumors may develop when transformed cells acquire the means to escape immunological host defense mechanisms. In *Immunology Today*, Vol. 5, No. 8, 1984, pp. 240–244, Snyderman et al discuss factors produced by tumor cells which depress macrophage-mediated functions, and the recent observation that these substances may be related to the retroviral structural envelope protein p15E.

Snyderman et al conclude that whereas oncogene activation can induce neoplastic transformation, the expression of a p15E-like protein may allow transformed cells to escape immune destruction. They suggest that the immunosuppressive activity of p15E could be important in promoting tumorigenesis in vivo if transformed cells acquired the ability to synthesize this product. This reference, however, does not identify or even suggest which p15E-like protein would have any such immunosuppressive activity. It simply discloses that p15E is a hydrophobic transmembrane protein (around 19,000 daltons) of the retroviral envelope which is synthesized as part of a precursor of molecular weight 80,000–90,000.

*Cianciolo et al, Nature,* Vol. 311, October 11, 1984, p. 515, disclose that there is a certain homology between the various p15E proteins and human T-cell leukaemia-lymphoma viruses, HTLV-I and HTLV-II, which occurs in a 26-amino acid sequence located in the p21 region of HTLV.

Cianciolo et al note, in particular, that the first ten amino acids of the region having homology are identical, and that this region of homology occurs in almost the same region of the p15E and p21 molecules. They conclude that the significance of these types of regions occurring in murine, feline and human retroviruses is not clear. They note that since dramatic immunosuppression is often associated with these viruses and that purified p15E is immunosuppressive in a variety of systems, it would be of particular significance to determine whether p21 of HTLV can also inhibit immune functions. But they provide no clue with respect to which part of this region of homology or which segment may possess any immune activity.

Immune modulators have applications in various fields involving the immune system. For example, they are useful in preventing graft rejection, preventing autoimmunity, or in aleviating inflammatory reactions. Immune modulators which have thus far been used have however frequently not been fully effective and have suffered from numerous undesirable and substantial side effects.

There is thus a need for novel immune modulators having a wide variety of applications without suffering from undesirable side effects.

SUMMARY OF THE INVENTION

Accordingly, it is an object of this invention to provide a novel class of immune modulators.

It is another object of this invention to provide a novel class of immune modulators which are effective without substantial side effects.

It is another object of this invention to provide a novel class of immune modulators which are useful in preventing graft rejection.

It is another object of this invention to provide a novel class of immune modulators which are useful in preventing or diminishing autoimmunity.

It is another object of this invention to provide a novel class of immune modulators which are useful as immunogens to elicit antibodies to block immunosuppression associated with naturally-occurring exogenous retroviral infections, activation of endogenous or retroviral proteins, or activation of cellular genes analagous to retroviral genes.

It is another object of this invention to provide a novel class of immune modulators which are useful to develop diagnostic assays for the presence in patient fluids of immunosuppressive proteins, or antibodies to such proteins.

The inventors have now surprisingly discovered a novel class of immunosuppressive peptides and analogs thereof which satisfy all of the objects of this invention outlined above, and other objects which will become apparent from a description of the invention given hereinbelow. These peptides are based on a 26 amino acid sequence, or part thereof, which is strikingly well conserved among a variety of retroviruses associated with immunosuppression. These viruses include murine and feline leukemia virus, human retrovirus (HTLV-I, II and III) and a simian virus which causes acquired immunodeficiency syndrome in monkeys. This invention thus relates to a novel class of immunosuppressive peptides having formula (I):

A-Gln-B-Arg-C-D-E-F-G-H-I-J-K-L-M-N-0 wherein:
A is Leu, Ala or Tyr;
B is Asn or Ala;
C is Arg, Leu or Ile;
D is Gly, Ala or Leu;
E is Leu or Ala;
F is Asp or Val;
G is Leu, Tyr, Glu or Ile;
H is Leu or Arg;
I is Phen, Leu , Tyr or Thr;
J is Leu, Trp or Ala;
K is Lys, Glu, Gln or Ala;
L is Glu, Gln or Asp;
M is Gly or Gln;
N is Gly or Gln; and
O is Leu, Val or Ile.

The above peptide, which can be used by itself or coupled to a carrier protein or coupled to a protein one wishes to render non-immunogenic or tolerogenic, possesses considerable immunosuppressive activity. The amino acid represented by A in formula (I) is an optional amino acid which can be used to facilitate coupling of the rest of the peptide to a carrier protein or other protein. A peptide corresponding to the peptide of formula (I) without amino acid A is identified herein as a peptide of formula (IV).

This invention also relates to a related peptide which is also imbued with significant immunosuppressive or imunoregulatory activity, and which comprises the following formula (II):

D-E-F-G-H-I-J-K-L-M-N-0-P-Q-R-S-T-U-V-W-X-Y wherein:
D is Gly, Ala or Leu;
E is Leu or Ala;
F is Asp or Val;
G is Leu, Tyr, Glu or Ile;
H is Leu or Arg;
I is Phe, Leu, Tyr or Thr;
J is Leu, Trp or Ala;
K is Lys, Glu, Gln or Ala;
L is Glu, Gln or Asp;
M is Gly or Gln;
N is Gly or Gln;
O is Leu, Val or Ile;
P is Cys or Leu;
Q is Ala, Lys, Gly or Leu;
R is Ala, Lys or Ile;
S is Leu, Ile, Phe or Trp;
T is Lys, Gln, Gly or Asn;
U is Glu, Leu or Cys
V is Glu, Gln, Thr, Ser or Lys;
W is Cys, Asn or Gly;
X is Cys, Arg, Phe, Tyr or Lys; and
Y is Phe, Cys or Leu.

The following peptide segment:

A Gln-B-Arg-C-, wherein B and C are as defined above, can be added to the left-hand side of the peptide of formula II to provide a 27-amino acid-long peptide of formula III.

The peptides of formula II and III which can be used by themselves or coupled to a carrier or coupled to a protein one wishes to render non-immunogenic or tolerogenic also possess considerable immunosuppressive activity.

The present invention further relates to the use of these peptides, exploiting their immunosuppressive activity.

BRIEF DESCRIPTION OF THE/DRAWINGS

A more complete appreciation of the invention and many of the attendant advantages thereof will be readily obtained as the same becomes better understood by reference to the following detailed description when considered in connection with the accompanying figures, wherein FIG. 1 illustrates the kinetics of CKS-17 inhibition of murine CTLL-2 cell proliferation. CKS-17 (ca. 15 μM) was added at time 0 and proliferation measured at the indicated times as described in Materials and Methods. Bars represent SEM of quadruplicate samples.

FIG. 2 illustrates the effects of CKS-17, homologous and non-homologous peptides, and a BSA control upon murine CTLL-2 cell proliferation. CTLL-2 cells were incubated with the indicated concentration of peptide of BSA control for 24 hour and proliferation measured as described in Materials and Methods. Bars represent SEM of (n) experiments for BSA control (16), CKS-17 (24), SP-9 (2), SP-74 (2), SP-16 (2), SP-70 (2), neurotensin (4).

FIG. 3 illustrates the effect of CKS-17 upon murine mixed leukocyte culture reactions. Cells were incubated for 3 days with the indicated concentration of CKS-17 (open bar) or BSA control (hatched bar) and proliferation measured as described in Materials and Methods. Proliferation was compared to cells incubated with media alone and bars reprsent SEM of 3 experiments.

FIG. 4 shows the effect of CKS-17 upon human mixed leukocyte culture reactions. Cells were incubated for the final 24 hours of a 6 day culture with the indicated concentration of CKS-17 (open bar) of BSA control (hatched bar) and proliferation measured as described in Materials and Methods. Proliferation was compared to cells incubated with media alone and bars represent SEM of 4 experiments.

FIG. 5 shows the dose response of the inhibition of monocyte $O_2^-$ release by CKS-17-BSA. The wheat germ agglutinin stimulated release of $O_2^-$ is shown for monocytes preincubated for 30 min with CKS-17-BSA (diagonal striped bar), BSA* (white bar), or buffer (black bar). Probabilities were calculated comparing buffer-treated cells to those treated with CKS-17-BSA using a t-test. Values represent mean (±SE) of a minimum of 11 experiments.

FIG. 6 illustrates that monocytes were incubated for the indicated time with 7.5 μM CKS-17 and then stimulated with 30 μg/ml of wheat germ agglutinin in the presence of 5 μg/ml cytochalasin E. $O_2^-$ *release was deter-* mined as the superoxide dismutase inhibitable reduction of cytochrome C measured after 5 in. Percent inhibition was calculated as:

$$\frac{(O_2^- \text{ release})_{control} - (O_2^- \text{ release})_{CKS\text{-}17\ treated}}{(O_2^- \text{ release})_{control}} \times 100$$

FIG. 7 illustrates the effects of CS-1, CS-3 BSA* and neurotensin upon CTLL-2 cell proliferation. Details as in legend to FIG. 2.

FIG. 8 illustrates the effects of CS-1, CS-3, BSA* and neurotensin upon OKT3-stimulated human lymphocyte proliferation. Details as in MATERIALS AND METHODS. Results represent averages of 5 experiments with standard errors (SE) indicated.

FIG. 9 shows the effects of CS-1, CS-3, BSA* and neurotensin upon human two-way mixed leukocyte culture reactions. Details as in legend to FIG. 4. Results represent averages of 4 experiments with S indicated.

FIG. 10 shows fluorescence reactivity of lymphocytes incubated with biotinylated CKS-17, BSA* or neurotensin and rhodamine-conjugated avidin.

FIG. 11 shows binding of [$^{125}$I]-CKS-17-BSA to cultured human lymphocytes. Human mononuclear cells were stimulated for 3 days with PHA, washed free of lectin and cultured for an additional 10 days in 10% of a human IL-2 preparation (Electronucleonics). The cells were washed and binding performed as described in Materials and Methods.

FIG. 12 shows Western Blot analysis of serum from rabbit immunized with CKS-17 not coupled to BSA. Various viruses (RLV, Rauscher leukemia virus; AKR; MoLV, Moloney leukemia virus; GLV, Gross leukemia virus; FeLV, feline leukemia virus) were detergent disrupted, electrophoresed on a SDS gel, electrophoretically transferred to activated aminophenylthioether (APT) paper, and nonspecific binding blocked by incubation of the paper in 5% BSA. Strips were cut and incubated for 2 hours at room temperature with (a) rabbit anti-p15E serum, 1:1,000 dilution, (b) normal rabbit serum, 1:200 dilution (c) rabbit anti-CKS-17 serum, 1:200 dilution. The strips were washed, incubated with [$^{125}$I]-labeled goat anti-rabbit IgG, washed, and put up for autoradiography.

FIG. 13 shows a structural model of p15E and construction of expression plasmids. Hatched regions are predominantly hydrophobic, unhatched regions are hydrophilic. The indicated restriction sites are located in the p15E coding region of the env gene of Moloney murine leukemia virus (M-MuLV) and were utilized for construction of the expression plasmids. The portion of the gene incorporated into each expression plasmid is indicated. Plasmids were constructed from subclones of pMo-env, a derivative of cloned proviral M-MuLV. After digestion of plasmids with the appropriate enzymes, the fragment ends were modified with the use of Klenow fragment, when necessary, to generate blunt ends and by the addition of synthetic Bam Hl linkers (New England Biolabs) of a size chosen to properly adjust the reading frame in each final construct. Fragments were isolated from gels and ligated into the Bam Hl site of expression vector pJG200 to generate pME-e1, pME-e2, pME-e3, and pME-e4.

DETAILED DESCRIPTION OF THE PREFERRED EMBODIMENTS

Figure 1:
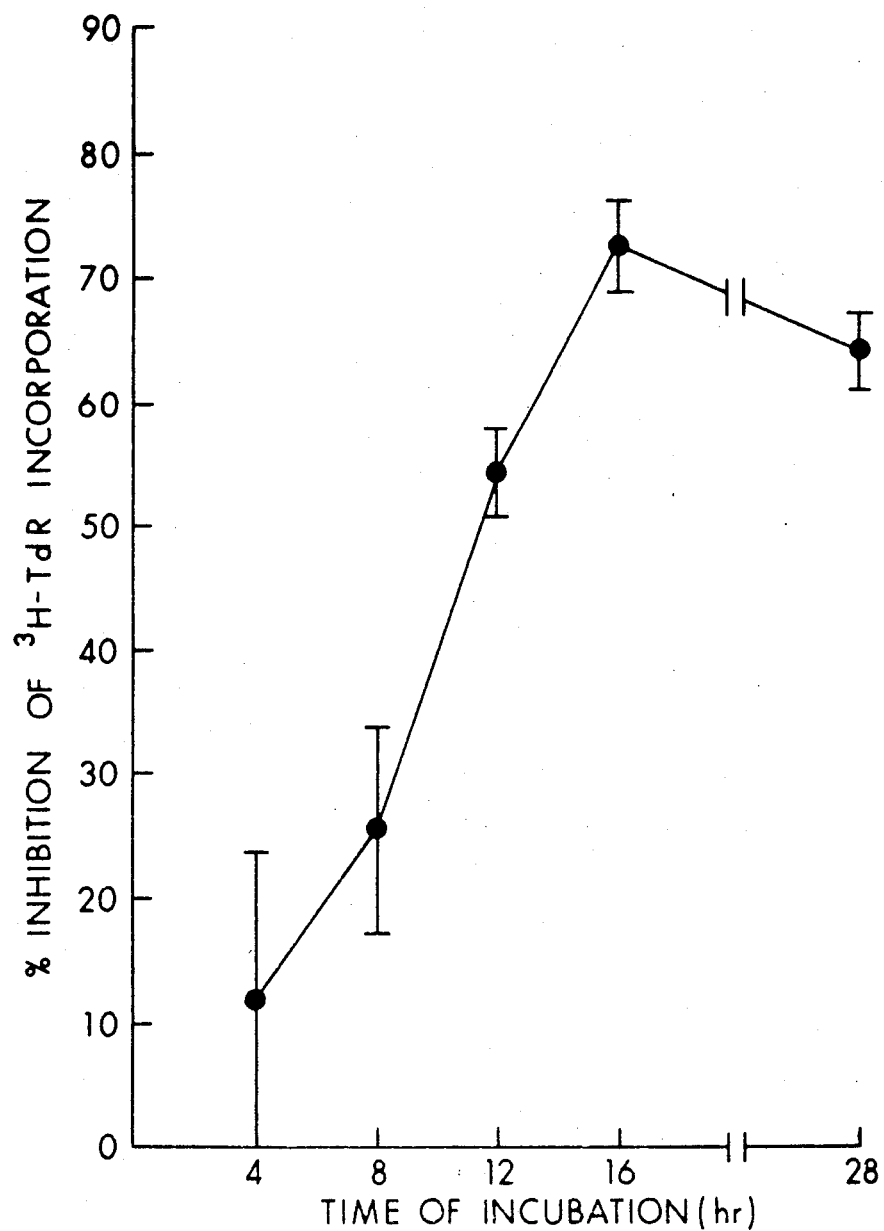

The present inventors have discovered that a class of polypeptides whose amino acid sequence are based on a region of homology contained within various retroviral envelope proteins possess high immunosuppressive activity. These peptides have a number of uses. For example, they are useful in preventing graft rejection, preventing or diminishing autoimmunity, in alleviating inflammatory reactions, as immunogens to elicit antibodies to block immunosuppression associated with naturally-occurring exogenous retroviral infections or neoplasia activation of endogenous retroviruses or retroviral proteins, or activation of cellular gene analogs to retroviral genes. They are also useful in the development of diagnostic assays for retroviral infections or cancer by monitoring the early appearance of peptide-related immunosuppressive proteins or of antibodies to such proteins.

More specifically, the peptides of the present invention have the following applications.

(1) Immunosuppressive Agents: The peptides have applications as immunosuppressive agents. They can be used to prevent the rejection of organ allografts or to alleviate some of the pathological effects of autoimmunity.

For example, diseases such as systemic lupus erythematosus, rheumatoid arthritis, scleroderma, dermatomyositis, polymyositis, unclassified connective diseases, autoimmune hemolytic anemia, idiopathic thrombocytopenic purpura, autoimmune thyroidits, polyarteritis nodosum, glomerulonephritis, uveitis, etc., all have immune-mediated components. Organ allograft rejection as well as many of the aforementioned autoimmune diseases have tissue destruction mediated at least in part by cell mediated immune reactions and the influx of inflammatory cells.

The immunosuppressive agents described herein have been shown in vitro to have dramatic effects on inhibiting cell-mediated immune reactions, as well as functions of inflammatory cells. This evidence shows that these immunosuppressive agents should be uniquely effective in preventing or diminishing tissue destruction as seen in allograft rejection and autoimmune diseases.

(2) Immunogens to Block Natural Immunosuppression: Since these peptides are related to retroviruses associated with immunosuppression in animals (feline leukemia virus and SRV-1, simian acquired immune deficiency syndrome retrovirus) and man (HTLV) they are useful as immunogens to elicit antibodies capable of blocking the immunosuppressive activity associated with such viruses or with neoplastic disease. In order to make immunogenic peptides capable of eliciting antibodies to the immunosuppressive peptides, the peptides are modified so that they are no longer immunosuppressive. This can be performed by substituting one or more of the amino acids within the sequence to obtain nonimmunosuppressive immunogenic forms of the peptides.

(3) Immunogens to Obtain Antibodies for Extracorporeal Absorption: The peptides are useful as immunogens to develop antibodies which can then be coupled to appropriate surfaces for use in extracorporeal absorption to remove immunosuppressive proteins from the sera of patients with retroviral infections or cancer.

Antibodies to the immunosuppressive proteins can be obtained using the immunogenic forms of the peptides to immunize animals such as goats, horses, sheep, rabbits, mice, etc. The antibodies are then purified by well known techniques and then coupled to solid phase matrices suitable for use in well known extracorporeal devices such as those currently used for plasmaphoresis.

Currently, staph protein A columns are being used to remove bilitarious circulating substance from cancer patients. In a similar fashion, the anti-immunosuppressive antibodies can be used to remove circulating immunosuppressive agents from cancer patients and thus make it more likely that they can reject their tumor cells.

(4) Anti-inflammatory Agents: The peptides are useful as anti-inflammatory agents capable of blocking the release of toxic oxygen products from phagocytes in inflammatory lesions. Such peptides can be injected locally in inflammatory loci such as the synovial fluid of patients with rheumatoid arthritis. They can moreover be administered by bronchial lavage to patients with adult respiratory distress syndrome. Systemic administration of the peptides will also allow them to be delivered to inflammatory sites throughout the body.

(5) Diagnostic agents: The peptides are useful in developing diagnostic tests for the appearance of immunosuppressive proteins in the sera or body fluids of patients with cancer, retroviral infections, or AIDS. Since recent studies have reported that patients with the AIDS prodrome (ARC) have immune dysfunction (failure to produce IL-2 or IFNγ), the ability to detect early circulating immunosuppressive proteins may be important not only for diagnosis but treatment as well.

For example, antibodies to the immunosuppressive peptides can be screened for in the serum of patients at risk. Moreover, using antibody to such peptides, one can screen for circulating immunosuppressive peptides in the circulation of at risk patients. Detection of antibody as well as circulating antigen can be carried out through the use of well known solid phase ELISA assays or other immunoabsorption techniques. These include Western blotting and radioimmunoprecipitation. The detection of circulating immunosuppressive activity would be followed by treatment to remove such circulating factors through immunoabsorptive techniques already described (see section 3).

(6) Tolerogenic agents: The peptides of this invention are useful in rendering proteins to which they are coupled non-immunogenic or inert to reactions with existing antibodies. Applications of this nature consist of coupling the peptide of this invention to a xenogenic protein which must be administered over a long period of time, such as anti-thymocyte globulin or murine monoclonal antibodies to tumor-specific antigens.

Additional proteins to which the peptides can be coupled include anti-Fc receptor antibodies, anti toxin antibodies (e.g., antibodies to tetanus toxin) and anti-idiotype antibodies. Coupling of peptides to proteins can be accomplished using carbodiimide or a number of other well known reagents for peptide coupling.

The present invention thus relates to a novel class of immunosuppressive peptides having a formula (I), (II), (III) or (IV). These peptides may be used by themselves, they may be coupled to carrier proteins, they can be coupled to proteins which one wishes to render non-immunogenic or tolerogenic, or they can be cross-linked. For coupling these peptides either to a carrier peptide or a peptide to be rendered non-immunogenic or tolerogenic, an additional leucine, alanine, tyrosine or other such amino acid well known in the rt can be added to the amino terminus to facilitate coupling.

The shorter peptides of formulae (I) and (IV) exhibit immunosuppressive activity when either (1) coupled to a carrier protein, such as for example, bovine serum albumin, human serum albumin, immunoglobulins or hormones (e.g., insulin), or (2) cross-linked to each other. The cross-linking between the peptides can be achieved, e.g., via carbodiimide treatment of the peptide.

The longer peptides of formulae (II) and (III) exhibit remarkable immunosuppressive activity by themselves. There is no need to couple these to a carrier protein or to cross-link with another protein, although these peptides can be also advantageously used coupled to either a carrier protein or another protein to be rendered non-immunogenic or tolerogenic.

For example, CKS-17 is immunosuppressive when coupled to human serum (HSA) albumin in addition to bovine serum albumin (BSA). Other carriers which can be used with any of the peptides of this invention include immunoglobulins or hormones (e.g., insulin) or serum proteins such as transferrin. A detailed exemplary coupling procedure is given in the MATERIALS AND METHODS section of this document.

The peptides of this invention have one of the following structure:

formula (I)

A-Gln-B-Arg-C-D-E-F-G-H-I-J-K-L-M-N-O formula (II)

D-E-F-G-H-I-J-K-L-M-N-O-P-Q-R-S-T-U-V-W-X-Y formula (III)

A-Gln-B-Arg-C-D-E-F-G-H-I-J-K-L-M-N-O-P-Q-R-S-T-U-V-W-X-Y formula (IV)

Gln-B-Arg-C-D-E-F-G-H-I-J-K-L-M-N-O where the variables A, B, C, D, E, F, G, H, I, J, K, L, M, N, O, P, Q, R, S, T, U, V, W, X and Y are as defined above.

Some preferred peptides are:

formula (Ia); (CKS-17)

Leu-Gln-Asn-Arg-Arg-Gly-Leu-Asp-Leu-Leu-Phe-Leu-Lys-Glu-Gly-Gly-Leu formula (Ib); (CS-1)

Ala-Glu.-Asn-Arg-Arg-Gly-Leu-Asp-Leu-Leu-Phe-Trp-Glu-Gln-Gly-Gly-Leu formula (Ic); (CS-2)

Tyr-Gln-Asn-Arg-Leu-Ala-Leu-Asp-Tyr-Leu-Leu-Ala-Ala-Glu-Gly-Gly-Val formula (Id); (CS-3)

Leu-Glu-Ala-Arg-Ile-Leu-Ala-Val-Glu-Arg-Tyr-Leu-Lys-Asp-Gln-Gln-Leu.

formula (Ie); (CS-SRV 17)

Leu-Gln-Asn-Arg-Arg-Gly-Leu-Asp-Leu-Leu-Thr-Ala-Glu-Gln-Gly-Gly-Ile formula (IIa); (CS-22)

Gly-Leu-Asp-Leu-Leu-Phe-Leu-Lys-Glu-Gly-Gly-Leu-Cys-Ala-Ala-Leu-Lys-Glu-Glu-Cys-Cys-Phe formula (IIb); (HTLV-I)

Gly-Leu-Asp-Leu-Leu-Phe-Trp-Glu-Gln-Gly-Gly-Leu-Cys-Lys-Ala-Leu-Gln-Glu-Gln-Cys-Arg-Phe formula (IIc); (HTLV-II)

Gly-Leu-Asp-Leu-Leu-Phe-Trp-Glu-Gln-Gly-Gly-Leu-Cys-Lys-Ala-Ile-Gln-Glu-Gln-Cys-Cys-Phe formula (IId); (feline)

Gly-Leu-Asp-Ile-Leu-Phe-Leu-Gln-Glu-Gly-Gly-Leu-Cys-Ala-Ala-Leu-Lys-Glu-Glu-Cys-Cys-Phe formula (IIe); (endog-22)

Ala-Leu-Asp-Tyr-Leu-Leu-Ala-Ala-Glu-Gly-Gly-Val-Cys-Gly-Lys-Phe-Asn-Leu-Thr-Asn-Tyr-Cys formula (IIf)

Gly-Leu-Asp-Leu-Leu-Thr-Ala-Glu-Gln-Gly-Gly-Ile-Cys-Leu-Ala-Leu-Gln-Glu-Lys-Cys-Cys-Phe formula (IIIa); Murine Virus Gln-Asn-Arg-Arg-Gly-Leu-Asp-Leu-Leu-Phe-Leu-Lys-Glu-Gly-Gly-Leu-Cys-Ala-Ala-Leu-Lys-Glu-Glu-Cys-Cys-Phe formula (IIIb); HTLV-I Virus Gln-Asn-Arg-Arg-Gly-Leu-Asp-Leu-Leu-Phe-Trp-Glu-Gln-Gly-Gly-Leu-Cys-Lys-Ala-Leu-Gln-Glu-Gln-Cys-Arg-Phe formula (IIIc); HTLV-II Virus Gln-Asn-Arg-Arg-Gly-Leu-Asp-Leu-Leu-Phe-Trp-Glu-Gln-Gly-Gly-Leu-Cys-Lys-Ala-Ile-Gln-Glu-Gln-Cys-Cys-Phe formula (IIId); Feline Virus Gln-Asn-Arg-Arg-Gly-Leu-Asp-Ile-Leu-Phe-Leu-Gln-Glu-Gly-Gly-Leu-Cys-Ala-Ala-Leu-Lys-Glu-Glu-Cys-Cys-Phe formula (IIIe); Endogenous Human Virus Gln-Asn-Arg-Leu-Ala-Leu-Asp-Tyr-Leu-Leu-Ala-Ala-Glu-Gly-Gly-Val-Cys-Gly-Lys-Phe-Asn-Leu-Thr-Asn-Tyr-Cys formula (IIIf); (monkey AIDS virus)

Gln-Asn-Arg-Arg-Gly-Leu-Asp-Leu-Leu-Thr-Ala-Glu-Gln-Gly-Gly-Ile-Cys-Leu-Ala-Leu-Gln-Glu-Lys-Cys-Cys-Phe formula (IVa)

Gln-Asn-Arg-Arg-Gly-Leu-Asp-Leu-Leu-Phe-Leu-Lys-Glu-Gly-Gly-Leu formula (IVb); (CS-1)

Gln-Asn-Arg-Arg-Gly-Leu-Asp-Leu-Leu-Phe-Trp-Glu-Gln-Gly-Gly-Leu formula (IVc); (CS-2)

Gln-Asn-Arg-Leu-Ala-Leu-Asp-Tyr-Leu-Leu-Ala-Ala-Glu-Gly-Gly-Val formula (IVd); (CS-3)

Gln-Ala-Arg-Ile-Leu-Ala-Val-Glu-Arg-Tyr-Leu-Lys-Asp-Gln-Gln-Leu.

Formula (IVe); (CS-SRV 17)

Gln-Asn-Arg-Arg-Gly-Leu-Asp-Leu-Leu-Thr-Ala-Glu-Gln-Gly-Gly-Ile

These peptides may be made to further possess sugar groups, normal serum components, lipids, phospholipids etc. Any of these can be bound directly onto the peptide in a manner well known in this art, with the only requirement being that the peptide structure be not affected to result in the loss of its immunosuppressive activity.

These novel peptides may be obtained by any method well known in this art. They may be synthesized using any of the well known peptide synthesis procedures; for example by using solid-phase Merrifield synthesis techniques. They may be obtained by fermentation of a genetically engineered microorganism capable of producing this peptide. Or a combination of genetic engineering and peptide synthesis may be used. They can also be obtained by purification hydrolysis of proteins of natural origin.

Other features of the invention will become apparent in the course of the following description of exemplary embodiments which are given for illustration of the invention and are not intended to be limiting thereof.

A peptide (CKS-17) was synthesized to correspond to the conserved region of p15E and subsequently tested for its effect on a variety of immune cell functions. In addition, peptides were synthesized to the corresponding conserved regions of the human retroviruses HTLV-I, -II and HTLV-III and subjected to similar testing. These peptides are identified as CS-1 and CS-3.

As the following data will show, all three peptides (CKS-17, CS-1, CS-3) are capable of inhibiting in vitro immune responses of human cells.

The three peptides (CKS-17, CS-1, and CS-3) synthesized to conserved regions of retroviral envelope proteins are capable of inhibiting the proliferative responses of human lymphocytes to mitogenic or alloantigen-induced stimulation. In addition, CKS-17 inhibits the respiratory burst activity of human monocytes preventing the release of toxic oxygen radicals.

CKS-17 binds to lymphocytes, perhaps through some form of receptor. Preliminary double-labeling studies have shown that CKS-17 binds to T4+ and T8+ lymphocytes, B cells, NK cells and phagocytes.

MATERIALS AND METHODS

Synthetic Peptides:

CKS-17(Leu-Gln-Asn-Arg-Arg-Gly-Leu-Asp-Leu-Leu-Phe-Leu-Lys-Glu-Gly-Gly-Leu), CS-1(Ala-Gln-Asn-Arg-Arg-Gly-Leu-Asp-Leu-Leu-Phe-Trp-Glu-Gln-Gly-Gly-Leu), CS-3 (Leu-Gln-Ala-Arg-Ile-Leu-Ala-Val-Glu-Arg-Tyr-Leu-Lys-Asp-Gln-Gln-Leu); two peptides with partial homology to CKS-17, SP-9(Glu-Val-Val-Leu-Glnpartial Asn-Arg-Arg-Gly-Leu-Asp-Leu-Leu) and SP-74(Gln-Tyr-Ala-Ala-Gln-Asn-Arg-Arg-Gly-Leu-Asp-Leu-Leu); and two nonhomologous peptides, SP-16(Pro-Val-Met-His-Pro-His-Gly-Ala-Pro-Pro-Asn-His-Arg-Pro-Trp-Gly-Met-Lys-Asn-Leu-Gln-Ala-Ile-Lys) and SP-70(Pro-Pro-Phe-Ser-Leu-Ser-Pro-Val-Pro-Thr-Leu) were synthesized using solid-phase Merrifield synthesis techniques, purified by ionexchange or gel-filtration and reversed-phase HPLC, an verified by HPLC and amino acid analysis. Neurotensin (Glu-Leu-Tyr-Glu-Asn-Lys-Pro-Arg-Arg-Pro-Tyr-Ile-Leu) was obtained commercially (Vega Biochemicals, Tucson, AZ). Peptides were coupled to the carrier protein bovine serum albumin (BSA; Sigma, St. Louis, MO) using carbodiimide by the following method: peptide (1.0 mM) and BSA (0.03 mM) were mixed in 0.1 M 1-Ethyl-3(3-Dimethylaminopropyl) Carbodimmide HCl for ca. 10 hr at 22° C and pH 5.0. An equal volume of 1.0 M glycine was added, the mixture rotated overnight at 4C, and then extensively dialyzed against Hank's Balanced Salt Solution containing 10 mM HEPES and adjusted to pH 7.2. For CS-1 and CS-3 the coupled peptides were dialyzed extensively against $H_2O$. Efficiency of coupling was determined using radiolabelled peptide as a tracer and averaged 30–40% resulting in conjugated material with a final peptide concentration of ca. 0.15 mM and a final BSA concentration of 0.015 mM. BSA alone was processed in an identical manner and used as an additional control identified as BSA*.

Cells and Cell Lines:

Human mononuclear cells were isolated from healthy laboratory volunteers by density gradient centrifugation of heparinized (10 units/ml) blood using Lymphocyte Separation Medium (LSM, Litton Bionetics, Charleston, S.C.). The cells were resuspended to $2 \times 10^6$ lymphocytets/ml in RPMI 1640 (Hazelton, Denver, PA) supplemented with 100 U/ml penicillin, 100 mcg/ml streptomycin, 2 mM L-glutamine, and 2% pooled human AB serum (K.C. Biological, Lenexa, KS) for Concanavalin A (Con A) and OKT3 assays of stimulated blastogenesis. For mixed leukocyte cultures (MLC) cells were resuspended in the same media supplemented with 1 mM Na pyruvate, 1% non-essential amino acids, and 2% fetal bovine serum (FBS) in place of human AB serum. Murine splenocytes were obtained from spleens of Balb/c or NIH/Swiss mice, washed and resuspended to $2 \times 10^6$ lymphocytes/ml in RPMI 1640 supplemented as above for the human MLC but containing $5 \times 10^{-5}$ M 2-mercaptoethanol. Murine CTLL-2 cells were obtained from the American Type Culture Collection and maintained in RPMI 1640 containing 5% FBS and 5% human interleukin 2 (IL-2) (Electronucleonics, Silver Spring, MD). Balb/3T3 and NIH/3T3 cell lines were generously provided by Drs. S. Aaronson and U. Rapp respectively.

Isolation of Monocytes

Mononuclear leukocytes were isolated from heparinized venous blood of normal volunteers by dextran sedimentation and Ficoll-Hypaque centrifugation and suspended at $1.2 \times 106$ monocytes/ml in Hanks's Balanced Salt Solution containing 10 mM Hepes, 4.2 mM sodium bicarbonate and 0.1% dextrose, pH=7.0 (HBSS).

Murine Cytoxic T Lymphocute (CTL) Proliferation Assay

Fifty $\mu$l of RPMI (6% FBS, 0% IL-2) containing 4 x $10^3$CTLL-2 cells was added to each well of a 96 well tissue culture plate (Falcon, Oxnard, CA). To each well was then added 50 $\mu$l of RPMI 1640 containing 3% human IL-2 50 $\mu$l of either RPMI or RPMI containing synthetic peptides. Cultures were then incubated for 24 hours at 37° C. in humidified 5% $CO^2$ Fifty $\mu$l of RPMI containing 1 $\mu$Ci of $^3$H-thymidine (6.7 Ci/mmole; New England Nuclear, Boston, MA) was added to each well for the final 4 hours of cultures. Cells were collected by filtration onto glass fiber filters and incorporated radioactivity determined by liquid scintillation spectrophotometry.

Murine Two-Way MLC

Fifty $\mu$l RPMI containing $1 \times 10^5$ Balb/c splenic lymphocytes and 50 $\mu$l containing $1 \times 10^5$ NIH/Swiss splenic lymphocytes were added to each well of a 96 well tissue culture plate. An additional 50 $\mu$l of RPMI containing peptide or no additives was added to each well and the cultures incubated for 3 to 5 days at 37° C in humidified 5% $CO^2$ Cultures were pulsed for 4 hr with 0.5 $\mu$Ci of $^3$H-thymidine in 50 $\mu$l of RPMI before harvesting onto glass fiber filters.

Human Two-Way MLC:

Fifty $\mu$l of RPMI containing $1 \times 10^5$ lymphocytes from each of two non-related individuals was added to each well of a 96 well tissue culture plate. An additional 50 $\mu$l of RPMI was added and cultures were incubated at 37° C. in humidified 5% $CO_2$ for 5 days. Fifty $\mu$l of RPMI containing either peptide or no addition was added for an additional 24 hr. During the final 4 hr of incubation each well was incubated with 25 $\mu$l of RPMI containing 0.5 $\mu$Ci of $^3$H-thymidine and incorporated radionucleotide determined as above.

Human Lymphocyte Responses to Con A or OKT3 Antibody

One hundred $\mu$l of RPMI containing $2 \times 10^5$ lymphocytes was added to each well of a 96 well tissue culture plate. Fifty μl of RPMI containing either peptide or no addition was added for 2 hr at 37° C followed by the addition of 50 μl of RPMI containing nothing or Con A (40 μg/ml) or OKT3 antibody (1:1000 dilution). The cultures were incubated for 72 hr at 37° C. in 5% humidified $CO_2$, pulsed with $^3$Hthymidine (0.,5 μCi/well, 4h.) and the incorporated radioactivity determined as described above. The concentration of OKT3 antibody used was previously determined to give 75–100% of a maximal response.

Effect of CKS-17 on Fibroblast Proliferation

CKS-17 was added at concentrations of 1:20, 1:40 and 1:80 to monolayers of Balb/3T3 or NIH/3T3 fibroblasts (ca. ⅓ confluent) in 96 well tissue culture plates. The cells were grown for an addition 2–3 days and pulsed with 1.0 μCi $^3$H-thymidine./well for the final 24 hours. The culture media was removed and the cells washed once before disruption with 0.5 ml of 0.5 N NaOH. The radiolabeled nucleic acids were then harvested onto glass fibe filters as described.

Measurement of Superoxide Anion ($O_2^-$) Release

Monocytes were aliquoted into 12×75 mm polypropylene tubes (Falcon, Oxnard, CA) and incubated at 37° C. with test materials for twenty minutes. Cytochalasin E was then added to give a final concentration of 5 μg/ml. Ten minutes later 1.5 mg/ml cytochrome C was added followed immediately by wheat germ agglutinin (WGA) to a final concentration of 30 μg/ml (1). Supernatants were removed after 5 min. for determination of $O_2^-$ dismutase-inhibitable reduction of cytochrome C (2).

Other Biological Assays

Oxygen consumption was measured with a Clark-type oxygen electrode using Gibson $O_2$ monitor at 37° C. Release of hydrogen peroxide ($H_2O_2$) was measured by oxidation of phenol red, as previously described (3). β-Glucuronidase secretion was determined by previously described methods (4) using a monocyte concentration of 8×10$^6$ monocyte/ml. For determination of monocyte polarization, monocytes were purified to >90% by countercurrent elutriation (Beckman Model J2-21M induction drive centrifuge, Beckman, Palo Alto, CA). The percentage of monocytes to undergo morphological polarization in response to the chemoattractant N-formyl-Met-Leu-Phe (FMLP) at 10$^{-8}$ M was determined as previously described (5). Monocyte chemotaxis was measured using two different techniques: the leading front technique into nitrocellulose filters (5.0 μm pore size, Millipore Corp., Bedford, MA) using the semiautomated method of Turner (6) and migration across a 5.0 μM pore size polycarbonate filter (Nucleopore Corp., Pleasanton, CA) in a modified Boyden chamber (7). Phagocytosis of antibody coated sheep erythrocytes by monocytes was measured as previously described (8).

Reagents

Hepes, cytochrome C (type VI), dimethylsulfoxide (DMSO), N-formyl-methionyl-leucyl-phenylalanine (FMLP) kept as a stock solution of 2 mg/ml in DMSO at −20° C., xanthine, xanthine oxidase, and phorbol myristate acetate (PMA) were obtained from Sigma Chemical Company, St. Louis, MO. Hank's Balanced Salt Solution was obtained from Gibco Laboratories, Grant Island, NY. Cytochalasin E was from Aldrich Chemical Company and kept as a stock solution of 2 mg/ml in DMSO at −20° C. Wheat germ agglutinin was from P.L. Biochemicals, Milwaukee, WI and kept as a stock solution of 2.5 mg/ml in water at −20° C. $O_2^-$ dismutase was from Diagnostic Data, Inc., Mountain View, CA.

Fluorescence Analysis Using Biotinylated CKS-17

CKS-17-BSA, BSA*, and neurotensin-BSA were all biotinylated using biotin-c-aminohexanoyl-Nbiotinylated hydroxysuccinimide ester. Human lymphocytes were obtained after monocyte depletion by plastic adherence of a LSM cell suspension. The cells were washed several times in Ca$^{++}$ and Mg$^{++}$ free HBSS pH 7.2 and resuspended in the same containing 5% BSA at a concentration of 10$^7$ cells/ml. One-tenth ml of cell suspension was incubated on ice for 30 min. with a 1:50 (ca. 3 μM) dilution of either biotinylated CKS-17-BSA, BSA*, neurotensin-BSA, or buffer alone. The cells were washed 4X, incubated for 30 min. on ice with a 1:50 dilution of rhodamine-labelled avidin, washed 4X, and resuspended in BSA-free HBSS containing 1% formaldehyde. The staihed cells were then examined using a Coulter EPICS V fluorescence-activated cell sorter.

Binding of Iodinated CKS-17-BSA to Lymphocytes

CKS-17-BSA was iodinated using Iodo-Beads (Pierce Chemical Co.) and carrier-free $^{125}$-I-Na (New England Nuclear) to a specific activity of 5–10 μCi/ug protein. Human mononuclear cells were stimulated for 3 days with PHA, washed free of lectin, cultured for 10 days with 10% of a human IL-2 preparation (electronucleonics) washed and resuspended to 5×10$^6$ cells/ml in phosphate-buffered-saline, pH 7.2 (PBS) containing 0.1% BSA. One-tenth ml of cell suspension was incubated in triplicate for 60 min. at room temperature in 12×75 mm polypropylene tubes containing ca. 250,000 cpm of [$^{125}$I]-CKS-17-BSA in 25 μl and 25 μl of either buffer or buffer containing >1000 fold excess of unlabeled CKS-17-BSA, CS-1-BSA, or CS-3-BSA. Binding was terminated and unbounded [$^{125}$I]-CKS-17-BSA removed by rapid (30 sec.) centrifugation of the cells through oil. The cell associated radioactivity was measured using a gamma radiation counter.

RESULTS

Effect of Synthetic Peptides on CTLL-2 Proliferation

Murine CTL cell lines are often used to measure the proliferative responses of lymphocytes to the mitogenic action of the lymphokine interleukin 2, also known as T cell growth factor (TCGF). Since p15E has been shown to inhibit the proliferation of such cells to IL-2, we tested CKS-17 for its effect upon the IL-2 dependent proliferation of murine CTLL-2 cells. Free (unconjugated) CKS-17 had no effect upon the CTLL-2cells. Since conformation might play an important role in the activity of the peptide, it and the other peptides were coupled to BSA as described. All data reported is therefore for peptide coupled to BSA. Table 1 contains results from two typical experiments and shows that incubation of CTLL-2-cells with increasing concentrations of CKS-17 resulted in a dose-dependent inhibition of cell proliferation as measured by 3H-thymidine uptake.

the average inhibition by CKS-17 at dilutions of 1:20, 1:40, and 1:80 was 49.6, 22.0, and 9.4% respectively.

Effect of CKS-17 on Murine and Human MLC

Figure 3:
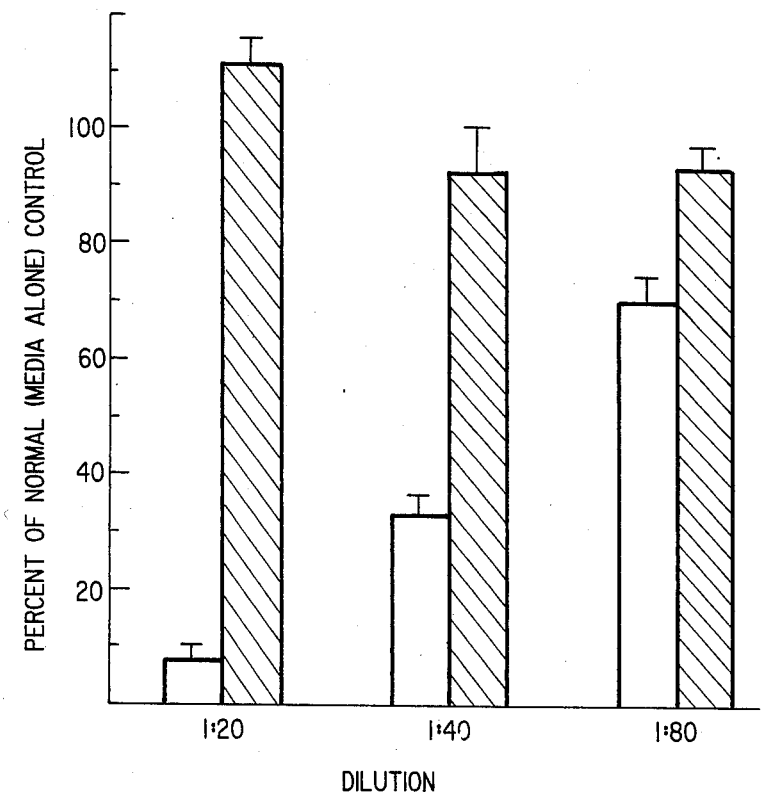

To determine if CKS-17 would inhibit the response of lymphocytes to allogeneic stimulation we tested its effect upon murine and human two-way mixed leukocyte cultures. As shown in FIG. 3, CKS-17 inhibited the

TABLE 1

Effects of CKS-17 on the Proliferation of Murine CTLL-2-Cells*

| Expt. | Material Tested | 1:20 | 1:40 | 1:80 |
|---|---|---|---|---|
| 1 | CKS-17 | 15,255 ± 277 (76)* | 42,827 ± 1386 (34) | 60,005 ± 1425 (7) |
|  | BSA | 67,108 ± 6050 (0) | 66,234 ± 1449 (0) | 65,281 ± 1782 (0) |
|  | Media Control = | 64,258 ± 2567 | | |
| 2 | CKS-17 | 10,950 ± 2171 (64) | 23,128 ± 3288 (24) | 29,980 ± 3490 (1) |
|  | BSA | 32,089 ± 2636 (0) | 31,805 ± 5480 (0) | 27,653 ± 2319 (8) |
|  | Media Control = | 30,289 ± 3796 | | |

*Measured as $^3$H—TdR-incorportation and expressed as CPM ± SD of quadruplicate samples.
+% inhibition
BSA which has undergone the same carbodiimide coupling reaction as the CKS-17.

At the highest concentration tested, ca. 7.3 μm, CKS-17 inhibited by 76 and 64% in the experiments illustrated. Under identical conditions the control BSA had little or no effect upon cell proliferation. The inhibition by CKS-17 was not due to either a short term toxic effect, as determined by trypan blue dye exclusion, or to interference with thymidine uptake since at a CKS-17 concentration of ca. 15 μM, maximal inhibition of CTLL-2 cell proliferation required 16 hours of incubation with the peptide (FIG. 1). The inhibition of CTLL-2 proliferation by CKS-17 could not be reversed by increasing the concentration of IL-2 twenty-fold.

Figure 2:
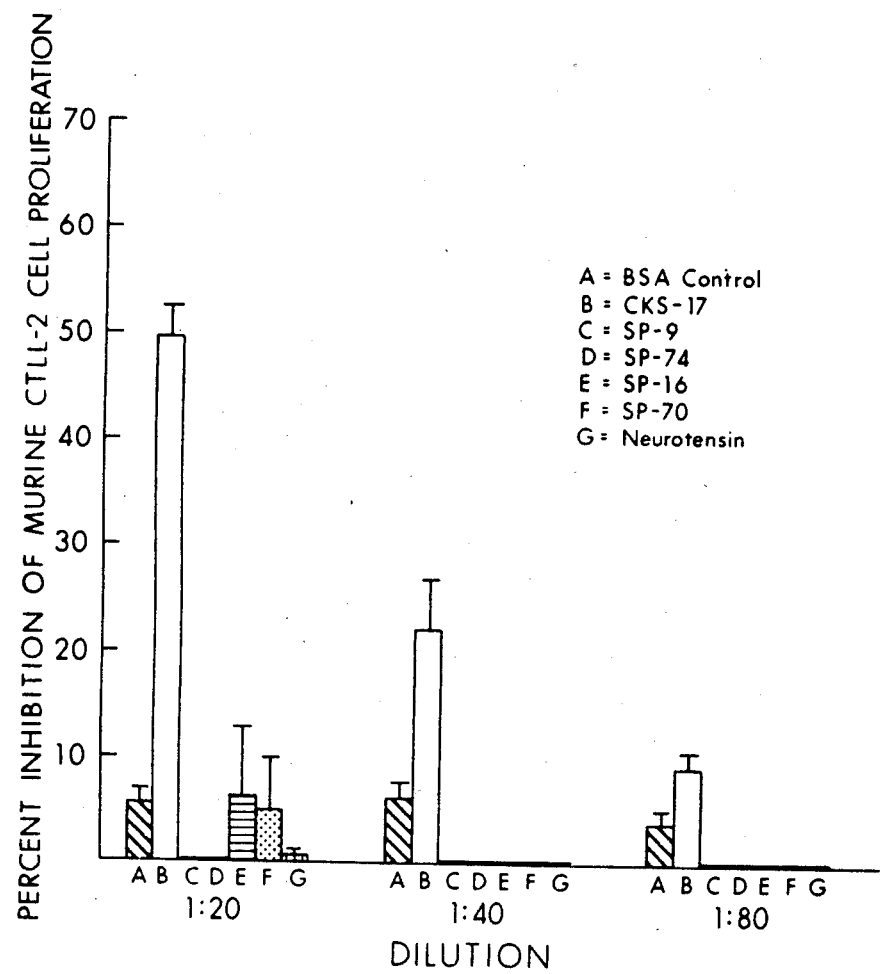
Figure 4:
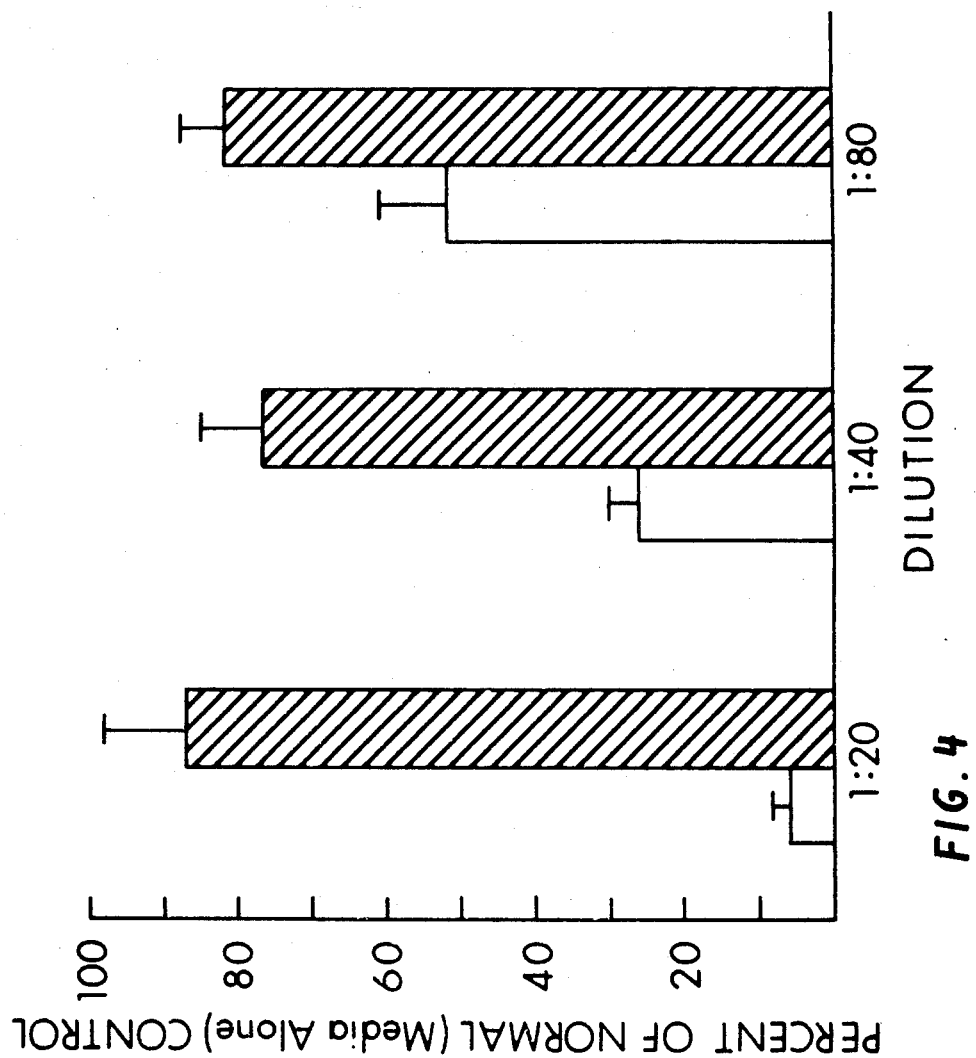

In order to determine if the inhibition of CTLL-2 cell proliferation by the CKS-17 peptide was specific for that sequence we incubated cells with either CKS-17, control BSA, the partially homologous viral peptides SP-9 or SP-74, the non-homologous peptides SP-16 or SP-70, or the non-homologous peptide neurotensin. As illustrated in FIG. 2, only the CKS-17 peptide had any significant effect upon CTLL-2 cell proliferation while the control BSA and the other five peptides had little or no effect under the same conditions. In 24 experiments 3 day murine MLC reaction in a dose dependent manner. In three different experiments the average inhibition of response at dilutions of 1:20, 1:30, and 1:80 was 94±2, 74±4 and 48±9% (mean±SEM) respectively. The control BSA had no significant effect upon cell proliferation under these same conditions. Five-day MLC reactions were also blocked by CKS-17. Similar results were obtained when the CKS-17 was tested for its effects upon a human two-way MLC reaction (FIG. 4). The average inhibition observed in four different experiments was 92±2, 64±11, and 18±3 (mean±SEM) at dilutions of 1:20, 1:40, and 1:80 respectively.

Effect of CKS-17 on Human Lymphocyte Responses to Con A

CKS-17 inhibited the proliferative responses of human lymphocytes to the mitogen Con A (Table 2).

TABLE 2

Effect of CKS-17 on the Proliferation of Human Lymphocytes Stimulated with Con A*

| Expt. | Material Tested | 1:10 | 1:20 | 1:40 | 1:80 |
|---|---|---|---|---|---|
| 1 | CKS-17 | 11,170 ± 3572 (88)+ | 38,132 ± 11,989 (58) | 38,085 ± 10,678 (58) | 46,815 ± 601 (48) |
|  | BSA± | 82,829 ± 5994 (9) | 83,140 ± 4075 (7) | 89,377 ± 1314 (2) | 84,416 ± 4229 (7) |
|  | Media Control = | 90,940 ± 6334 | | | |
| 2 | CKS-17 | 34,601 ± 3914 (66) | 62,445 ± 3602 (38) | 83,154 ± 4422 (17) | 95,395 ± 45 (5) |
|  | BSA | 101,810 ± 13,329 (0) | 93,788 ± 13,137 (7) | 90,543 ± 7746 (10) | 105,768 ± 40 (0) |
|  | Media Control = | 100,581 ± 4299 | | | |

*Measured as $^3$H—TdR-incorporation and expressed as CPM ± SD of quadruplicate samples.
+% Inhibition
± BSA which has undergone the same carbodiimide coupling reaction as the CKS-17-BSA.

The incorporation of $^3$H-thymidine was blocked by up to 88% at a 1:20 dilution (ca. 7.5μM) of CKS-17. The BSA control had little or not effect under similar conditions. Addition to the peptide 24 hr. after addition of the mitogen resulted in comparable levels of inhibition suggesting that the peptide was not directly interfering with the mitogen.

Effect of CKS-17 on Fibroblast Proliferation

In order to test whether the inhibition of proliferation by CKS-17 was specific for lymphoid cells we tested its effect on proliferating Balb/3T3 and NIH/3T3 at dilutions similar to those used in the aforementioned assays. The CKS-17 had no effect upon $^3$H-thymidine incorporation by either cell type when cultured for either 2 or 3 days in the presence of the peptide.

Effect of CKS-17 on the Monocyte Respiratory Burst

Figure 5:
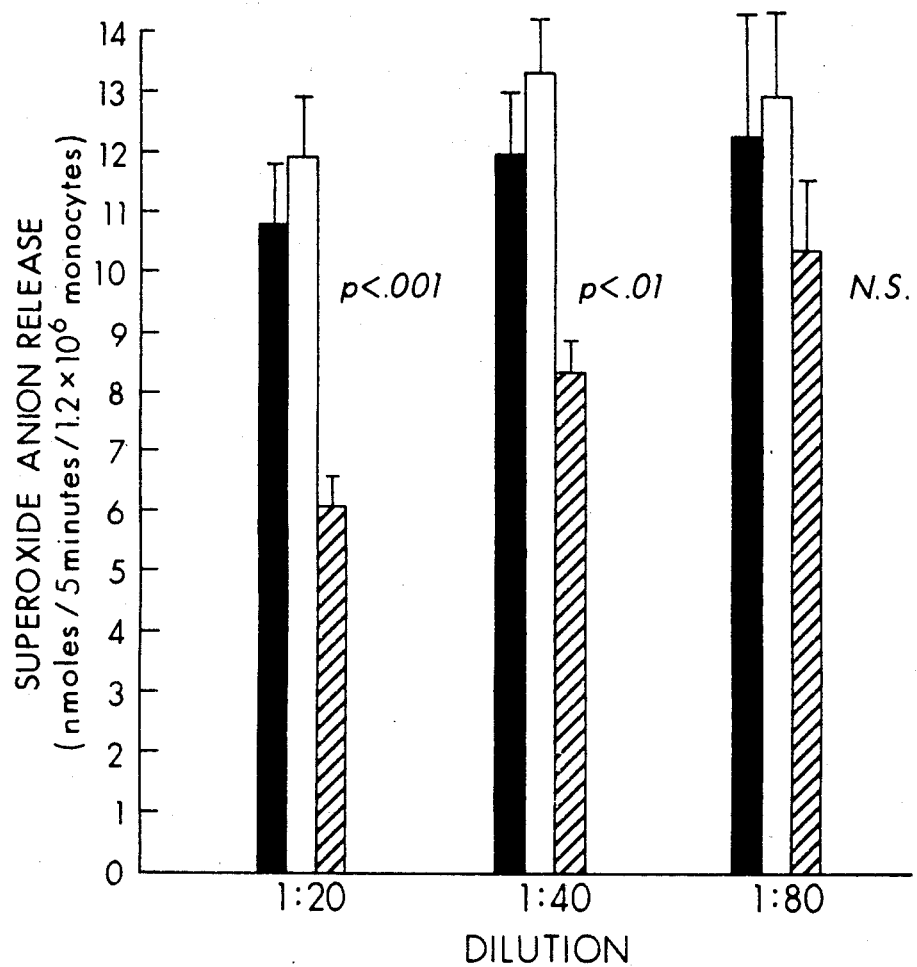
Figure 6:
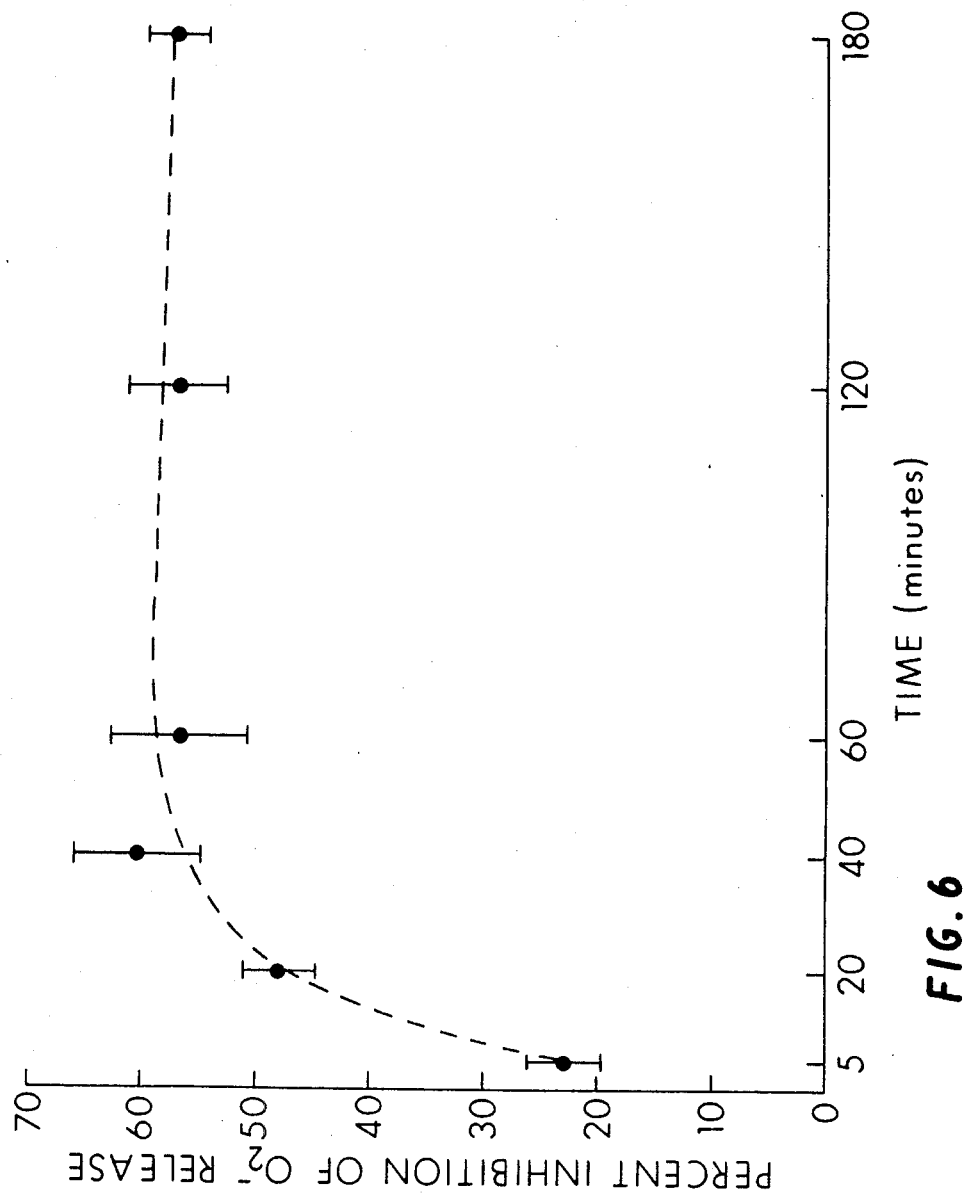

Treatment of human monocytes with WGA and cytochalasin E stimulated substantial release of $O_2^-$ which was inhibited by CKS-17-BSA. FIG. 5 shows $O_2^-$ release by monocytes preincubated for thirty minutes with CKS-17-BSA compared to monocytes preincubated with buffer only or with BSA*. CKS-17-BSA produced significant (p<0.001) dose related suppression of $O_2^-$ release with a 1:20 dilution of CKS-17-BSA resulting in a 46.5±2.3% inhibition. CKS-17-BSA did not affect the baseline release of $O_2^-$ by monocytes. The coupled peptide caused a similar degree of inhibition of $O_2^-$ release when PMA (50 ng/ml) was the stimulant (data not shown). Suppression of $O_2^-$ release by CKS-17-BSA was detected within fifteen minutes after exposure of monocytes to the peptide and reached a maximal level within one hour (FIG. 6). The maximum degree of suppression continued for at least two more hours. When the CKS-17-BSA was washed from the monocytes after a thirty minute preincubation and the cells then stimulated with WGA thirty minutes later, the amount of suppression was the same as that of cells from which the CKS-17-BSA was not washed.

To determine if CKS-17-BSA affected other parameters of the respiratory burst, WGA plus cytochalasin E were used to stimulated monocytes. At a 1:40 dilution, preincubation of monocytes with CKS-17-BSA caused a suppression of oxygen uptake (66±7%) and a suppression of hydrogen peroxide release (22.0±0.6 to 4.6±0.2 nmoles/30 min/10$^6$ monocytes) compared to monocytes preincubated with BSA*. Baseline activity of neitehr $O_2$ consumption nor $H_2O_2$ release was affectd by CKS-17-BSA. CKS-17-BSA contained no scavenger activity for $O_2^-$ generated by the interaction of xanthine and xanthine oxidase.

Effect of Other Synthetic Peptides on Monocyte $O_2^-$ Release

Each of the five other synthetic peptides was coupled to BSA in a manner identical to that used for the coupling of CKS-17. None caused suppression of $O_2^-$ release of monocytes when stimulated by WGA (Table 3).

TABLE 3

Effect of Synthetic Peptides on Monocyte $O_2^-$ Release Stimulated by WGA*

| Peptide Coupled to BSA | Dilution 1:20 | 1:40 |
|---|---|---|
| | $O_2^-$ Release+ | |
| None | 11.9 ± 1.0 | 13.3 ± 0.9 |
| CKS-17 | 6.0 ± 0.5 | 8.3 ± 0.5§ |

TABLE 3-continued

Effect of Synthetic Peptides on Monocyte $O_2^-$ Release Stimulated by WGA*

| Peptide Coupled to BSA | Dilution 1:20 | 1:40 |
|---|---|---|
| | $O_2^-$ Release+ | |
| Neurotensin | 12.3 ± 0.4 | 13.5 ± 0.2 |
| SP-9 | 10.6 ± 0.3 | 12.4 ± 0.5 |
| SP-16 | 9.8 ± 0.2 | 12.4 ± 0.6 |
| SP-70 | 10.7 ± 0.5 | 11.6 ± 0.2 |
| SP-74 | 10.7 ± 0.4 | 12.5 ± 0.5 |

*Values represent mens (± SE) of a minmum of 4 experiments.
+nmoles/5 minues/1.2 × 10$^6$ monocytes.
 p < 0.001 compared to monocytes incubated with buffer alone.
§p < 0.01 compared to monocytes incubated with buffer alone.

Effect of CKS-17-BSA on Other Monocyte Functions

Table 4 shows the effect of preincubation of CKS-17-BSA on other monocyte functions.

TABLE 4

Human Monocyte Function After Incubation with CKS-17-BSA or BSA*

| Function Tested+ | CKS-17-BSA | BSA* |
|---|---|---|
| Phagocytosis | 6.6 = 0.9% | 6.5 ± 0.5% |
| Chemotaxis to FMLP (nitrocellulose filter) | 108.0 ± 7.0 μm | 114.0 ± 7.0 μm |
| Chemotaxis to FMLP (polycarbonate filter) | 19.5 ± 0.9 cells/O.I.F. | 21.4 ± 1.3 cells/O.I.F. |
| Polarization | 58.0 ± 1.0% | 60.0 ± 2.0% |
| β-Glucuronidase secretion | 47.2 ± 5.5% | 44.8 ± 6.5% |

*BSA which had undergone the same carbodiimide coupling procedure as the CKS-17-BSA.
+All functions were tested at a 1:40 dilution of CKS-17-BSA or BSA* and values represent mean (±SE) of a minimum of two experiments.

The synthetic peptide did not affect chemotaxis or morphological polarization to the chemoattractant FMLP, lysosomal enzyme secretion (β-glucuronidase) to WGA, or phagocytosis of opsonized sheep erythrocytes. Two indices of monocyte toxicity, LDH release and trypan blue dye exclusion, were not affected by exposure of the cells to CKS-17-BSA at any concentrations used.

Effects of CS-1 and CS-3 on CTLL-2-Proliferation

Figure 7:
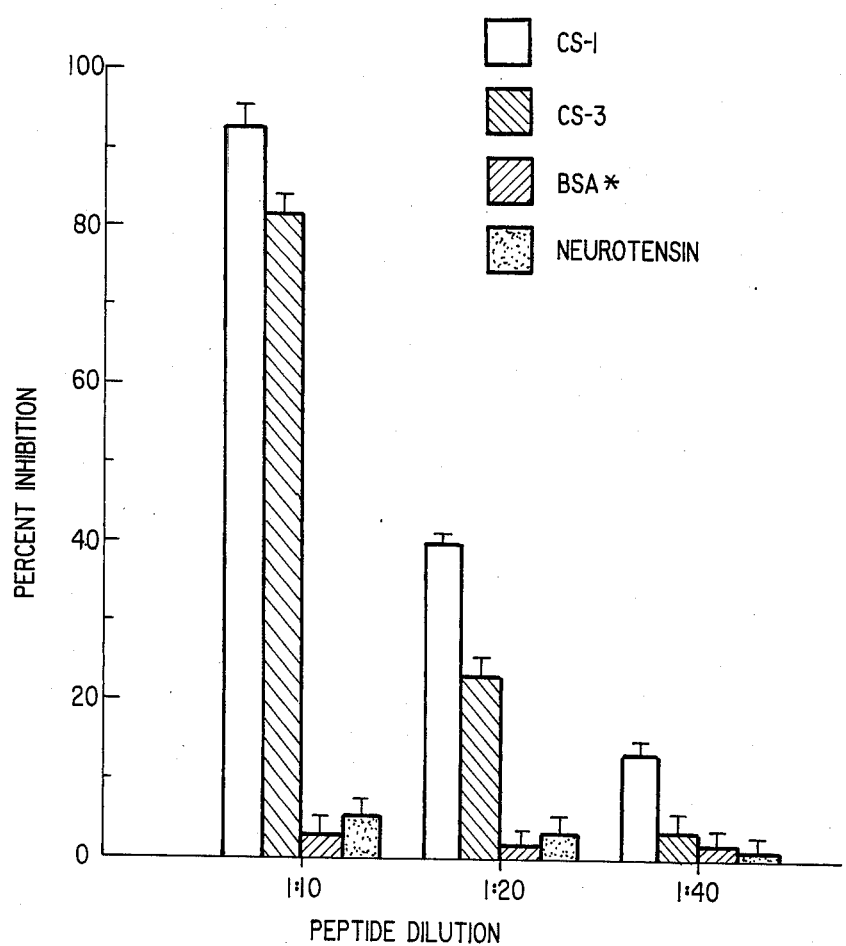

To determine if the synthetic peptides CS-1 and CS-3, homogolous to HTLV-I, -II and HTLV-III, had similar activity to that observed for CKS-17, the peptides were tested for their effects upon the proliferation of murine CTLL-2 cells. As shown in FIG. 7, in 5 experiments CS-1 inhibited CTLL-2 proliferation by an average of 92.8, 39.8, and 13.4% at concentrations of ca. 15, 7.5 and 3.75 μM while in 4 experiments CS-3 inhibited by an average of 81.8, 23.2, and 3.5% at similar concentrations. The BSA control or neurotensin-BSA had no significant effect as previously demonstrated.

Effect of CS-1 and CS-3 on OKT3-Stimulated Human Lymphocyte Proliferation

Figure 8:
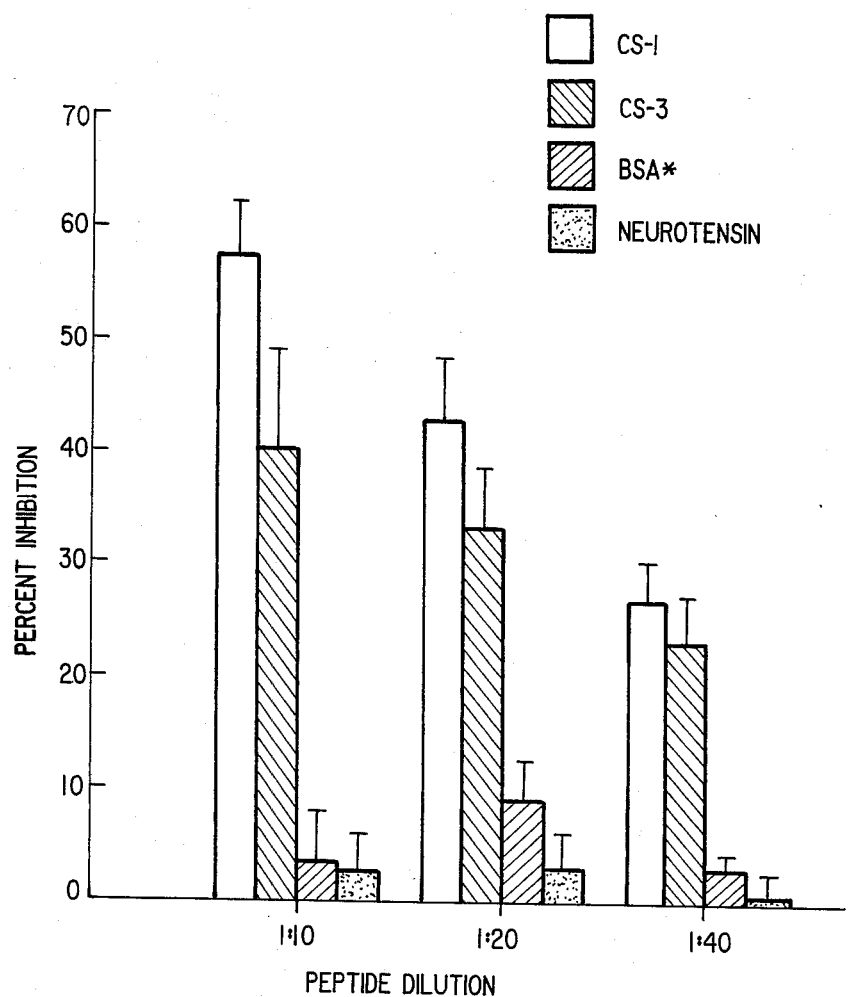

In order to determine if CS-1 and CS-3 could inhibit the proliferation of human lymphocytes to the mitogenic action of OKT3 (αT3) antibody, cells were incubated for 3 days in the presence or absence of peptide with a concentration of OKT3 previously determined to give 75-100% of maximal stimulation. As shown in FIG. 8, in 5 experiments at concentrations of ca. 15, 7.5, and 3.75 μM, CS-1 inhibited lymphocyte proliferation by an average of 57.6, 42.8, and 26.8% while CS-3 inhibited proliferation by 40.4, 33.4, and 23.2% respectively. Control BSA or neurotensin-BSA had no significant effects at these concentrations.

Effects of CS-1 and CS-3 on Human Two-Way Mixed Leukocyte Cultures

Figure 9:
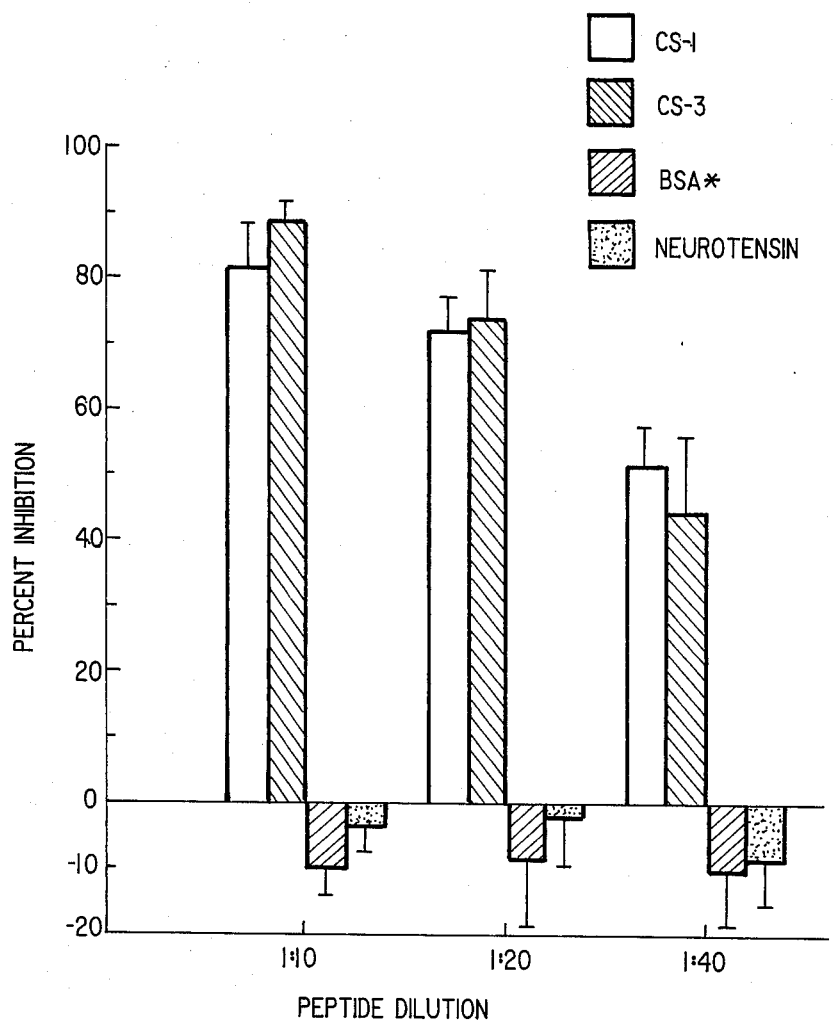

In order to determine if alloantigen-induced proliferative responses could also be inhibited by CS-1 and CS-3, the peptides were added at concntrations of 15, 7.5, and 3.75 μM to 6-day two-way human mixed leukocyte cultures. As shown in FIG. 9, in 4 experiments CS-1 inhibited by an average of 81.8, 72.2, and 51.8% while CS-3 inhibited by an average of 88.5, 74.0 and 44.5% respectively at the same concentrations. There was no inhibition by either the control BSA or the neurotensin-BSA.

Fluorescence Using Biotinylated CKS-17-BSA

Figure 10:
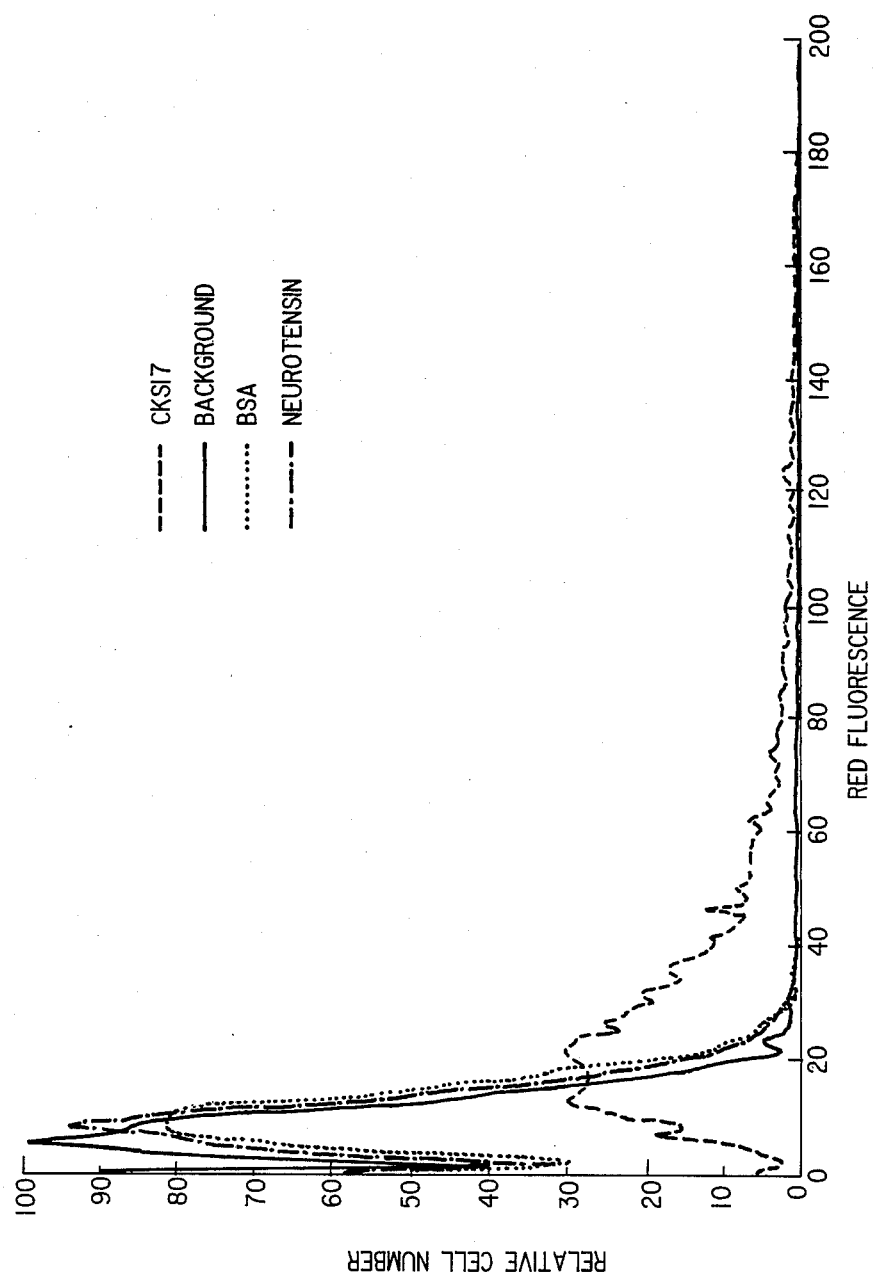

Human lymphocytes were incubated with either buffer alone, biotinylated CKS-17-BSA, biotinylated BSA*, or biotinylated neurotensin-BSA and then with rhodamine-labelled avidin and examined by FACS. As shown in FIG. 10, there was no increase in fluorescent staining of cells incubated with BSA* or neurotensin-BSA compared to the buffer control. In contrast, ca. 70% of the lymphocytes incubated with the CSK-17-BSA exhibited increased fluorescence compared to any of the controls.

Binding of [$^{125}$I]-CKS-17-BSA to Human Lymphocytes

Figure 11:
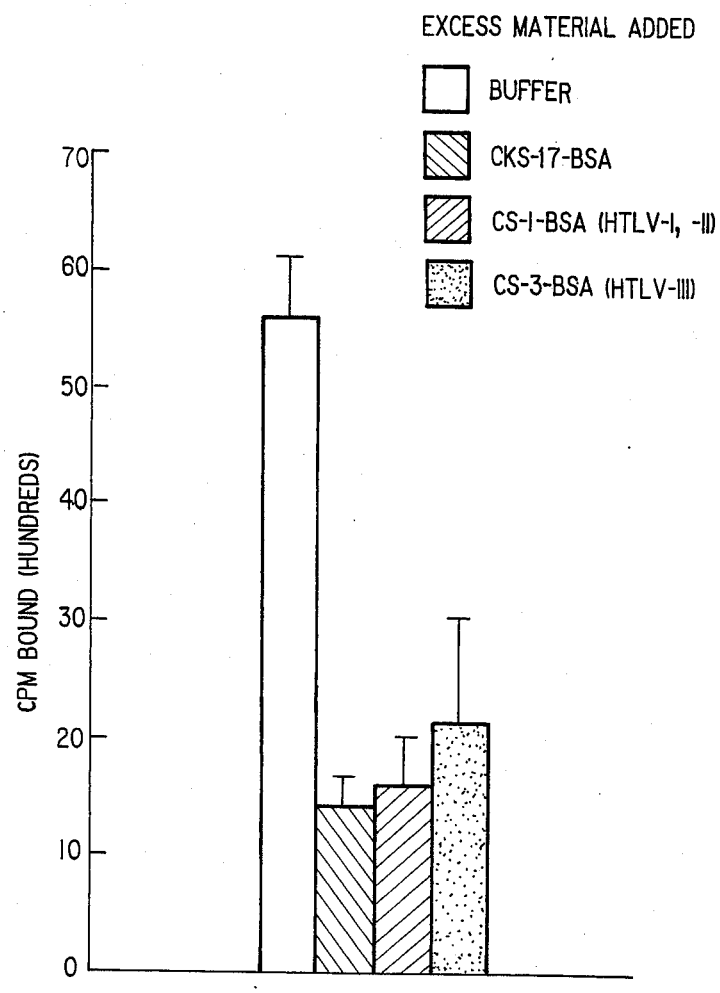

In order to verify the results obtained by fluorescent-staining we tested the ability of [$^{125}$I]-labelled CKS-17-BSA to bind to human lymphocytes. As shown by FIG. 11, the iodinated peptide bound to the lymphocytes and the binding could be inhibited by an excess of either unlabelled CKS-17 or CS-1 or CS-3 suggesting that there is specificity to the binding.

Immunization of Rabbits with CKS-17 or CKS-17-BSA

Figure 12:
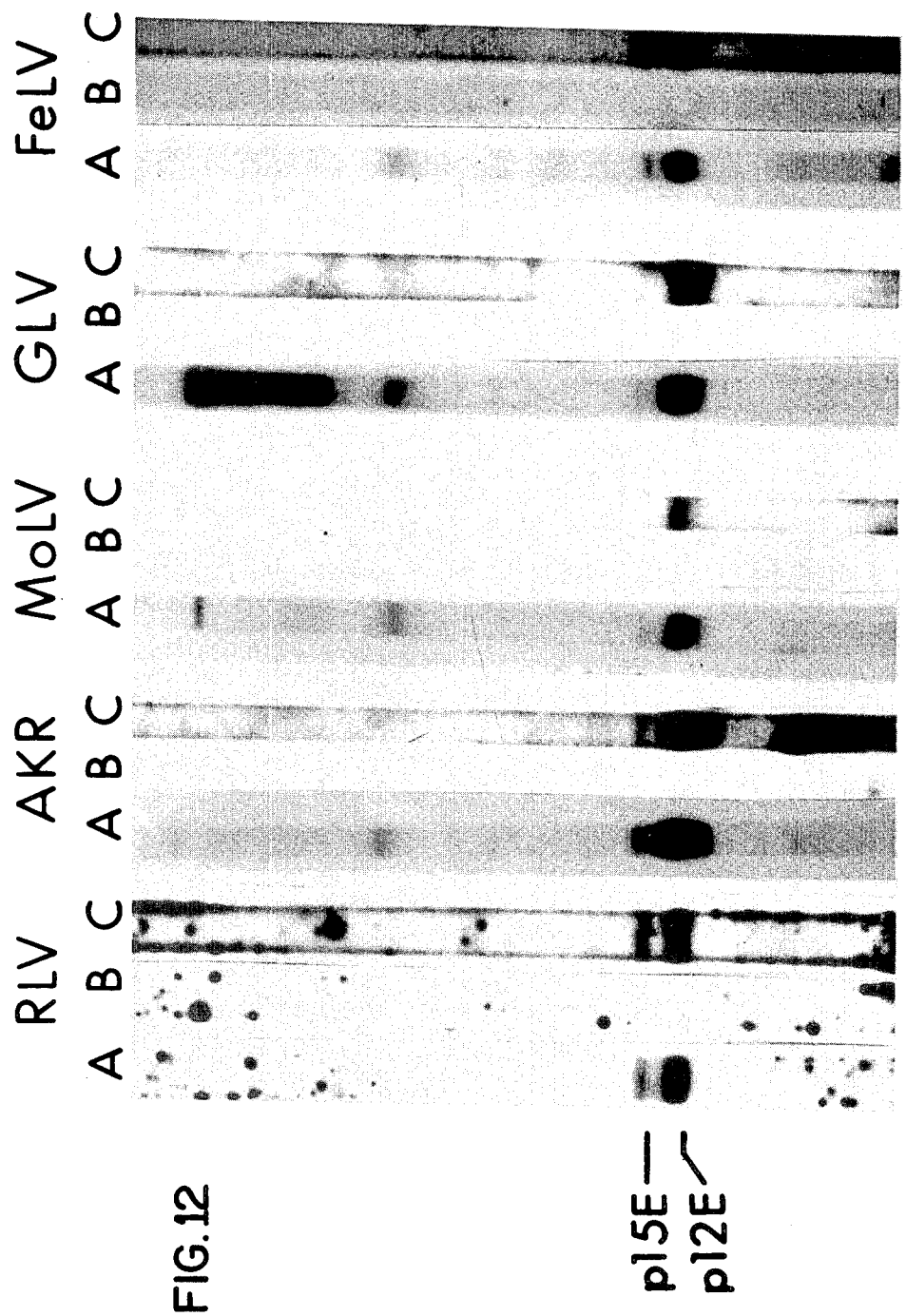

Immunization of rabbits with CKS-17-BSA failed to elicit antibodies to the conjugate or to the free peptide. This is not a result of the peptide sequence being non-immunogenic since immunication of rabbits with peptide not conjugated to BSA elicited antibodies which react with free peptide and the native viral protein from which the amino acid sequence was derived. As shown in FIG. 12 the anti-peptide serum shows the same reactivity toward viral p15E (and its degradation product, p12E) as does a polyclonal serum raised against native protein.

The failure to elicit antibodies in rabbits immunized with CKS-17-BSA (the biologically active form) is interesting. Antibodies are produced which react with both native BSA and the BSA control (BSA*) which has undergone the same carbodiimide coupling reaction. These antibodies also recognize BSA which is coupled to neurotensin. Furthermore, commercial antisera to BSA show the same pattern of reactivity as does the anti-CKS-17-BSA serum. This suggests that when the biologically-active peptides (e.g., CKS-17 and CS-1 and CS-3 are coupled to BSA they may no longer be immunogenic and they are not immunoreactive with antibodies to BSA. This loss of immunoreactivity is not confined to the "native" structures of the peptide-BSA conjugates. When CKS-17-BSA, CS-1-BSA, or CS-3-BSA are electrophoresed on a denaturing (SDS) gel and electroblotted to nitrocellulose paper they still fail to react with antiserum to BSA. The above data makes clear that coupling of these biologically-active peptides (CKS-17, CS-1, CS-3) to the carrier protein BSA renders the carrier protein inert for reactions with existing antibodies to the carrier protein.

Production of the proteins of this invention by genetic engineering techniques

The following is an example of the application of genetic engineering techniques to obtain the proteins of this invention. The production of p15E-based proteins is provided in detail below. This technology however can be applied to the production of any of the proteins of this invention by following methodology well known in this art.

Inactivated murine, feline, and human retrovirus particles inhibit lymphocyte functions in vitro and fractionated retroviral protein of the same molecular weight as the transmembrane envelope protein p15E of murine and feline leukemia viruses has suppressive activity in vitro and in vivo. p15E and related molecules can also function as immunosuppressive agents in neoplastic disease since extracts prepared from carcinogen-induced primary murine tumors and human malignant effusions contain inhibitors which can be specifically absorbed by anti-p15E monoclonal antibodies. Thus p15E and antigenically related proteins can contribute to the pathogenesis of abnormal immune function associated with retroviral infection and neoplasia.

Efforts to directly study the biological activity of retroviral p15E have been hampered by its limited availability in retrovirus preparations and by its extreme hydrophobicity. Atempts to remove detergent or denaturant from purified p15E preparations, a prerequisite for many types of biological applications and/or studies, leads to aggregation and precipitation. We have now overcome these problems of studying and using this potentially biologically important protein by constructing a plasmid which directs the expression, in *E. coli*, of only the major hydrophilic region of the p15E protein.

Figure 13:
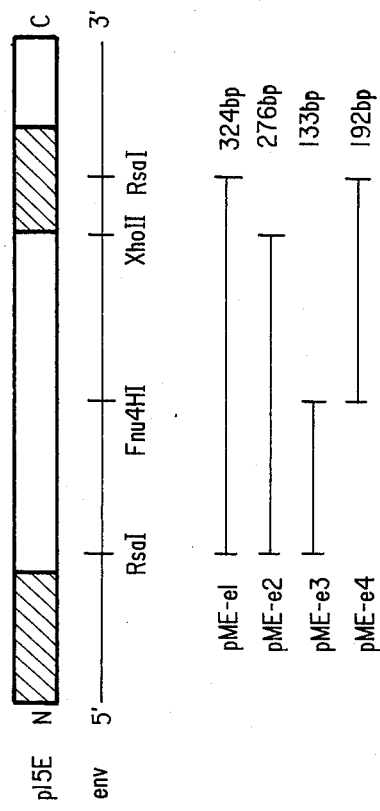

Analysis of the sequence of murine p15E suggests that its overall hydrophobicity may be due to two distinct regions in the molecule. FIG. 13 shows schematically the organization of the p15E protein as deduced from hydrophobicity-hydrophilicity plots of p15E sequences. p15E consists of four distinct sequential regions: an N-terminal hydrophobic sequence, a larger hydrophilic sequence, a second hydrophobic domain, and a final short C-terminal hydrophilic region. This general structure is typical for the transmembrane envelope proteins of mammalian type C retroviruses. Three of the four regions are thought to play assignable roles. The N-terminal hydrophobic region is likely extracellular and may serve as a domain for interaction with the exterior envelope glycoprotein and with the membrane of target cells during virus infection. The second hydrophobic domain is assumed to be the membrane-spanning region. The C-terminal hydrophilic region is probably cytoplasmic and may interact with internal viral core proteins during virus assembly. The function of the central large hydrophilic region of p15E is unknown. That it may be important for the biological activity of p15E is suggested by a high degree of conservation among mammalian retroviruses of a sequence internal to this region. In addition, the hydrophilic region is probably located on the surface of the virion or the cell expressing p15E and thus would be accessable for interaction with the surrounding immunological environment.

The env gene of cloned proviral Moloney murine leukemia virus was used to construct prokaryotic expression plasmids (FIG. 13). Four constructs were made which included different portions of the coding sequence of the major hydrophilic region and the downstream hydrophobic domain (pME-e1, pME-e2, pME-e3 and pME-e4). The construct (pME-e2) which most nearly isolated the entire hydrophilic region yielded the most stable protein product. This might indicate that the hydrophilic region encoded by pME-e2 actually defines one or more structural domains, since the stability of foreign proteins expressed in E. coli appears to be related in part to the ability of the protein to fold properly into a native configuration. The pME-e2 fusion protein was further shown to react with each of five different anti-p15E monoclonal antibodies. Because of its appreciable level of expression (ca. 20 mg per liter of induced culture, based on determinations of β-galactosidase activity) and the stability of the protein, pME-e2 was chosen for use in protein purification and immunological studies.

Purification of the recombinant protein was simplified by the design of the expression plasmid, a derivative of pJG200. pME-e2 directs the synthesis of a tripartate fusion protein, consisting of p15E sequence and enzymatically active β-galactosidase connected by a short segment of collagen. This permitted purification of the fusion protein with affinity resins specific for β-galactosidase and for p15E. The p15E portion of the purified fusion protein was liberated from β-galactosidase by digestion with collagense and was further purified by anti-p15E affinity chromatography. The resulting product was highly (ca. 99%) pure by scanning densitometry of a coomassie-blue stained SDS polyacrylamide gel. The final p15E derivative proved to be soluble in physiological buffer (Hank's balanced salt solution). In the absence of detergent, this material remained in the supernatant after centrifugation at 100,000×1 hr.

The p15E derivative was tested for biological activity using, as an indicator, the interleukin-2 (IL-2) dependent CTLL-2 murine T cell line. Dose-dependent inhibition of CTLL-2 cell proliferation was observed, reaching 90% inhibition at 4 μM of p15E derivative. In contrast, the β-galactosidase component of the cleaved fusion protein, purified under nearly identical conditions as the p15E derivative, gave no significant inhibition at equivalent protein concentrations. The potency of the recombinant p15E derivative is comparable to that reported for the presumed p15E isolated from feline leukemia virus.

The references referred to numerically in the specification are given below.
1. Nakagawara, A., K. Kayashima, R. Tamada, K. Onou, K. Ikeda, and K. Inokuchi. 1979. Sensitive and rapid method for determination of superoxide-generating activity of blood monocytes and its use as a probe for monocyte function in cancer patients. Gann. 70:829.
2. McPhail, L. C., C. C. Clayton, and R. Snyderman. 1984. the NADPH oxidase of human polymorphonuclear leukocytes:evidence for regulation by multiple signals. J. Biol. Chem. 259:5768–5775.
3. Pick, E., and Y. Kaisari. 1980. A simple colorimetric method for the measurement of hydrogen peroxide produced by cells in culture. Journal of Immunological Methods 38:161.
4. Brittinger, G., R. Hirshhorn, S. D. Douglas, and G. Weissmann. 1968. Studies on lysosomes: characterization of a hydrolaserich fraction from human lymphoytes. J. Cell. Biol. 377:394.
5. Cianciolo, G. J. and R. Snyderman. 1981. Monocyte responsiveness to chemotactic stimuli in vitro is a property of a subpopulation of human mononuclear cells which can respond to multiple chemoattractants. J. Clin. Invest. 67:60–68.
6. Turner, S. R. 1979. An automated chemotaxis data acquisition system. J. Immunol. Methods 28:355.
7. Lohr, K. M., and R. Synderman. 1981. In vitro methods for the study of macrophage chemotaxis. In Manual of Macrophage Methodology. H. B. Herscowitz, et al., editors. Marcel Dekker, Inc. New York. 303–313.
8. Synderman, R., M. C. Pike, D. G. Fischer, and H. S. Koren. 1977. Biologic and biochemical activities of continuous macrophage cell lines P38801 and J774.1. J. Immunol. 119:2060–2066.

Obviously, numerous modifications and variations of the present invention are possible in light of the above teachings. It is therefore to be understood that within the scope of the appended claims, the invention can be practiced otherwise than as specifically described herein.

What is claimed as new and desired to be secured by Letter Patent of the United States is:

1. A peptide having immunosuppressive or immunoregulatory activity, comprising the formula (I):

A-Gln-B-Arg-C-D-E-F-G-H-I-J-K-L-M-N-O wherein:
A is Leu, Ala or Tyr;
B is Asn or Ala;
C is Arg, Leu or Ile;
D is Gly, Ala or Leu;
E is Leu or Ala;
F is Asp or Val;
G is Leu, Tyr, Glu or Ile;
H is Leu or Arg;
I is Phe, Leu, Tyr or Thr;
J is Leu, Trp or Ala;
K is Lys, Glu, Gln or Ala;
L is Glu, Gln or Asp;
M is Gly or Gln;

N is Gly or Gln; and
O is Leu, Val or Ile.

2. A peptide having immunosuppressive or immunoregulatory activity, comprising the formula (IV):

Gln-B-Arg-C-D-E-F-G-H-I-J-K-L-M-N-O, wherein:
B is Asn or Ala;
C is Arg, Leu or Ile;
D is Gly, Ala or Leu;
E is Leu or Ala;
F is Asp or Val;
G is Leu, Tyr, Glu or Ile;
H is Leu or Arg;
I is Phe, Leu, Tyr or Thr;
J is Leu, Trp or Ala;
K is Lys, Glu, Gln or Ala;
L is Glu, Gln or Asp;
M is Gly or Gln;
N is Gly or Gln; and
O is Leu, Val or Ile.

3. The peptide of claim 1, wherein the said peptide is coupled to a carrier protein.

4. The peptide of claim 2, wherein the said peptide is coupled to a carrier protein.

5. The peptide of claim 1, wherein the said peptide is coupled to a protein to be rendered nonimmunogenic or tolerogenic.

6. The peptide of claim 2, wherein the said peptide is coupled to a protein to be rendered nonimmunogenic or tolerogenic.

7. The peptide of claim 1, said peptide having the formula: Leu-Gln-Asn-Arg-Arg-Gly-Leu-Asp-Leu-Leu-Phe-Leu-Lys-Glu-Gly-Gly-Leu.

8. The peptide of claim 1, said peptide having the formula: Ala-Gln-Asn-Arg-Arg-Gly-Leu-Asp-Leu-Leu-Phe-Trp-Glu-Gln-Gly-Gly-Leu.

9. The peptide of claim 1, said peptide having the formula: Tyr-Gln-Asn-Arg-Leu-Ala-Leu-Asp-Tyr-Leu-Leu-Ala-Ala-Glu-Gly-Gly-Val.

10. The peptide of claim 1, said peptide having the formula: Leu-Gln-Ala-Arg-Ile-Leu-Ala-Val-Glu-Arg-Tyr-Leu-Lys-Asp-Gln-Gln-Leu.

11. The peptide of claim 1, said peptide having the formula: Leu-Gln-Asn-Arg-Arg-Gly-Leu-Asp-Leu-Leu-Thr-Ala-Glu-Gln-Gly-Gly-Ile.

12. A peptide having immunosuppressive or immunoregulatory activity, comprising the formula:

D-E-F-G-H-I-J-K-L-M-N-O-P-Q-R-S-T-U-V-W-X-Y wherein:
D is Gly, Ala or Leu;
E is Leu or Ala;
F is Asp or Val;
G is Leu, Tyr, Glu or Ile;
H is Leu or Arg;
I is Phe, Leu, Tyr or Thr;
J is Leu, Trp or Ala;
K is Lys, Glu, Gln or Ala;
L is Glu, Gln or Asp;
M is Gly or Gln;
N is Gly or Gln;
O is Leu, Val or Ile;
P is Cys or Leu;
Q is Ala, Lys, Gly or Leu;
R is Ala, Lys or Ile;
S is Leu, Ile, Phe or Trp;
T is Lys, Gln, Gly or Asn;
U is Glu, Leu or Cys;
V is Glu, Gln, Thr, Ser or Lys;
W is Cys, Asn or Gly;
X is Cys, Arg, Phe, Tyr or Lys; and
Y is Phe, Cys or Leu.

13. The peptide of claim 12, wherein the said peptide is coupled to a carrier protein or a protein to be rendered non-immunogenic or tolerogenic.

14. The peptide of claim 12, said peptide having the formula: Gly-Leu-Asp-Leu-Leu-Phe-Leu-Lys-Glu-Gly-Gly-Leu-Cys-Ala-Ala-Leu-Lys-Glu-Glu-Cys-Cys-Phe.

15. The peptide of claim 12, said peptide having the formula: Gly-Leu-Asp-Leu-Leu-Phe-Trp-Glu-Gln-Gly-Gly-Leu-Cys-Lys-Ala-Leu-Gln-Glu-Gln-Cys-Arg-Phe.

16. The peptide of claim 12, said peptide having the formula: Gly-Leu-Asp-Leu-Leu-Phe-Trp-Glu-Gln-Gly-Gly-Leu-Cys-Lys-Ala-Ile-Gln-Glu-Gln-Cys-Cys-Phe.

17. The peptide of claim 12, said peptide having the formula: Gly-Leu-Asp-Ile-Leu-Phe-Leu-Gln-Glu-Gly-Gly-Leu-Cys-Ala-Ala-Leu-Lys-Glu-Glu-Cys-Cys-Phe.

18. The peptide of claim 12, said peptide having the formula: Ala-Leu-Asp-Tyr-Leu-Leu-Ala-Ala-Glu-Gly-Gly-Val-Cys-Gly-Lys-Phe-Asn-Leu-Thr-Asn-Tyr-Cys.

19. The peptide of claim 12, said peptide having the formula: Gly-Leu-Asp-Leu-Leu-Thr-Ala-Glu-Gln-Gly-Gly-Ile-Cys-Leu-Ala-Leu-Gln-Glu-Lys-Cys-Cys-Phe.

20. The peptide of claim 12, said peptide having the formula: Leu-Ala-Val-Glu-Arg-Tyr-Leu-Lys-Asp-Gln-Gln-Leu-Leu-Gly-Ile-Trp-Gly-Cys-Ser-Gly-Lys-Leu.

21. A peptide having immunosuppressive or immunoregulatory activity, comprising one of the following amino acid sequence:

Gln-Asn-Arg-Leu-Asp-Tyr-Leu-Leu-Ala-Ala-Glu-Gly-Gly-Val-Cys-Gly-Lys-Phe-Asn-Leu-Thr-Asn-Tyr-Cys,

Gln-Asn-Arg-Arg-Gly-Leu-Asp-Leu-Leu-Thr-Ala-Glu-Gln-Gly-Gly-Ile-Cys-Leu-Ala-Leu-Gln-Glu-Lys-Cys-Phe, or

Gln-Ala-Arg-Ile-Leu-Ala-Val-Glu-Arg-Tyr-Leu-Lys-Asp-Gln-Gln-Leu-Leu-Gly-Ile-Trp-Gly-Cys-Ser-Gly-Lys-Leu.

22. A composite peptide having immunosuppressive activity, comprising one of the following amino acid sequence:

Gln-Asn-Arg-Arg-Gly-Leu-Asp-Leu-Leu-Phe-Leu-Lys-Glu-Gly-Gly-Leu-Cys-Ala-Ala-Leu-Lys-Glu-Glu-Cys-Cys-Phe,

Gln-Asn-Arg-Arg-Gly-Leu-Asp-Leu-Leu-Phe-trp-Glu-Gln-Gly-Gly-Leu-Cys-Lys-Ala-Leu-Gln-Glu-Gln-Cys-Arg-Phe, or Gln-Asn-Arg-Arg-Gly-Leu-Asp-Leu-Leu-Phe-Trp-Glu-Gln-Gly-Gly-Leu-Cys-Lys-Ala-Ile-Gln-Glu-Gln-Cys-Cys-Phe, coupled to a carrier protein or another protein which is to be rendered non-immunogenic or tolerogenic.

23. The peptide of claim 22, said peptide comprising the following amino acid sequence: Gln-Asn-Arg-Arg-Gly-Leu-Asp-Leu-Leu-Phe-Leu-Lys-Glu-Gly-Gly-Leu-Cys-Ala-Ala-Leu-Lys-Glu-Glu-Cys-Cys-Phe.

24. The peptide of claim 22, said peptide comprising the following amino acid sequence: Gln-Asn-Arg-Arg-Gly-Leu-Asp-Leu-Leu-Phe-Trp-Glu-Gln-Gly-Gly-Leu-Cys-Lys-Ala-Leu-Gln-Glu-Gln-Cys-Arg-Phe.

25. The peptide of claim 22, said peptide comprising the following amino acid sequence: Gln-Asn-Arg-Arg-Gly-Leu-Asp-Leu-Leu-Phe-Trp-Glu-Gln-Gly-Gly-Leu-Cys-Lys-Ala-Ile-Gln-Glu-Gln-Cys-Cys-Phe.

26. The peptide of claim 21, said peptide having the formula: Gln-Asn-Arg-Leu-Ala-Leu-Asp-Tyr-Leu-Leu-Ala-Ala-Glu-Gly-Gly-Val-Cys-Gly-Lys-Phe-Asn-Leu-Thr-Asn-Tyr-Cys.

27. The peptide of claim 21, said peptide having the formula: Gln-Asn-Arg-Arg-Gly-Leu-Asp-Leu-Leu-Thr-Ala-Glu-Gln-Gly-Gly-Ile-Cys-Leu-Ala-Leu-Gln-Glu-Lys-Cys-Cys-Phe.

28. The peptide of claim 21, said peptide having the formula: Gln-Ala-Arg-Ile-Leu-Ala-Val-Glu-Arg-Tyr-Leu-Lys-Asp-Gln-Gln-Leu-Leu-Gly-Ile-Trp-Gly-Cys-Ser-Gly-Lys-Leu.

29. A composite protein having immuno-suppressive or immuoregulatory activity, said composite protein comprising two peptides comprising the formula (I):

A-Gln-B-Arg-C-D-E-F-G-H-I-J-K-L-M-N-O cross-linked to each other, wherein:
A is Leu, Ala or Tyr;
B is Asn or Ala;
C is Arg, Leu or Ile;
D is Gly, Ala or Leu;
E is Leu or Ala;
F is Asp or Val;
G is Leu, Tyr, Glu or Ile;
H is Leu or Arg;
I is Phe, Leu, Tyr or Thr;
J is Leu, Trp or Ala;
K is Lys, Glu, Gln or Ala;
L is Glu, Gln or Asp;
M is Gly or Gln;
N is Gly or Gln; and
O is Leu, Val or Ile.

30. A composite protein having immunosuppressive or immunoregulatory activity, said composite protein comprising two peptides comprising the formula (IV):

Gln-B-Arg-C-D-E-F-G-H-I-J-K-L-M-N-O cross-linked to each other, wherein:
B is Asn or Ala;
C is Arg, leu or Ile;
D is Gly, Ala or Leu;
E is Leu or Ala;
F is Asp or Val;
G is Leu, Tyr, Glu or Ile;
H is Leu or Arg;
I is Phe, Leu, Tyr or Thr;
J is Leu, Trp or Ala;
K is Lys, Glu, Gln or Ala;
L is Glu, Gln or Asp;
M is Gly or Gln;
N is Gly or Gln; and
O is Leu, Val or Ile.

31. A composite peptide comprising the amino acid sequence Leu-GLn-Asn-Arg-Arg-Gly-Leu-Asp-Leu-Leu-Phe-Leu-Lys-Glu-Gly-Gly-Leu coupled to a carrier protein or another protein which is to be rendered non-immunogenic or tolerogenic.

32. The composite peptide of claim 31, wherein the said carrier protein comprises bovine serum albumin, human serum albumin, an immunoglobulin or a hormone.

33. The composite peptide of claim 31, wherein the said carrier protein comprises bovine serum albumin or human serum albumin.

34. The composite peptide of claim 31, wherein the said carrier protein comprises human serum albumin.

35. A composite peptide having immunosuppressive or immunoregulatory activity, comprising one of the following amino acid sequences:
Gln-Asn-Arg-Leu-Ala-Leu-Asp-Tyr-Leu-Leu-Ala-Ala-Glu-Gly-Gly-Val-Cys-Gly-Lys-Phe-Asn-Leu-Thr-Asn-Tyr-Cys;
Gln-Asn-Arg-Arg-Gly-Leu-Asp-Leu-Leu-Thr-Ala-Glu-Gln-Gly-Gly-Ile-Cys-Leu-Ala-Leu-Gln-Glu-Lys-Cys-Cys-Phe; or
Gln-Ala-Arg-Ile-Leu-Ala-Val-Glu-Arg-Tyr-Leu-Lys-Asp-Gln-Gln-Leu-Leu-Gly-Ile-Trp-Gly-Cys-Ser-Gly-Lys-Leu,
coupled to a carrier protein or another protein which is to be rendered non-immunogenic or tolerogenic.

* * * * *

UNITED STATES PATENT AND TRADEMARK OFFICE
CERTIFICATE OF CORRECTION

PATENT NO. : 4,822,606
DATED : APRIL 18, 1989
INVENTOR(S) : Snyderman, et al.

It is certified that error appears in the above-identified patent and that said Letters Patent is hereby corrected as shown below:

Column 1, line 5, after the title insert -- This invention was made with government support under Grant No. CA346717 awarded by the National Institutes of Health. The government has certain rights in this invention.--

Signed and Sealed this

Twelfth Day of October, 1993

Attest:

BRUCE LEHMAN

Attesting Officer

Commissioner of Patents and Trademarks